(12) United States Patent
Anazawa et al.

(10) Patent No.: US 10,175,172 B2
(45) Date of Patent: Jan. 8, 2019

(54) MULTICOLOR DETECTION DEVICE

(71) Applicant: HITACHI HIGH-TECHNOLOGIES CORPORATION, Tokyo (JP)

(72) Inventors: Takashi Anazawa, Tokyo (JP); Satoshi Takahashi, Tokyo (JP); Motohiro Yamazaki, Tokyo (JP); Yoshitaka Kodama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/548,432

(22) PCT Filed: Feb. 3, 2015

(86) PCT No.: PCT/JP2015/052933
§ 371 (c)(1),
(2) Date: Aug. 3, 2017

(87) PCT Pub. No.: WO2016/125244
PCT Pub. Date: Aug. 11, 2016

(65) Prior Publication Data
US 2018/0024061 A1    Jan. 25, 2018

(51) Int. Cl.
*G01N 21/64* (2006.01)
*G01J 3/44* (2006.01)
(Continued)

(52) U.S. Cl.
CPC ....... *G01N 21/6452* (2013.01); *C12Q 1/6869* (2013.01); *G01J 3/4406* (2013.01);
(Continued)

(58) Field of Classification Search
CPC .. G01N 21/6452; C12C 1/6869; G01J 3/4406
See application file for complete search history.

(56) References Cited

U.S. PATENT DOCUMENTS 6,437,345 B1 *  8/2002  Bruno-Raimondi ........................ G01N 21/474
250/252.1
2003/0226756 A1  12/2003  Inaba et al.
(Continued)

FOREIGN PATENT DOCUMENTS

JP    10-513553 A    12/1998
JP    2005-519309 A    6/2005
(Continued)

OTHER PUBLICATIONS

Takanobu Haga, et al., "Simultaneous four-color imaging of single molecule fluorophores using dichroicmirrors and four charge-coupled devices", Review of Scientific Instruments 82, 023701, 2011.
(Continued)

*Primary Examiner* — Hugh H Maupin
(74) *Attorney, Agent, or Firm* — Mattingly & Malur, PC

(57) ABSTRACT

A multicolor detection device includes: a condensing lens array 17 in which a plurality of condensing lenses 18, each of which turns light emitted from each of a plurality of light emitting points 1 individually into parallel light beams, are arranged, the light emitting points being arranged in a light emitting point array; at least one spectroscopic element on which the parallel light beams are incident in parallel, the at least one spectroscopic element being common; and at least one sensor on which light beams spectrally separated by the spectroscopic element are incident in parallel, the at least one sensor being common.

20 Claims, 15 Drawing Sheets

(51) Int. Cl.
*C12Q 1/6869* (2018.01)
*G01N 27/447* (2006.01)
(52) U.S. Cl.
CPC ... *G01N 21/6428* (2013.01); *G01N 27/44721* (2013.01); *G01N 27/447* (2013.01); *G01N 2021/6441* (2013.01); *G01N 2021/6471* (2013.01); *G01N 2021/6478* (2013.01)

(56) References Cited

U.S. PATENT DOCUMENTS

| 2004/0105266 A1* | 6/2004 | Kim ................ H04N 9/3117 362/293 |
| 2011/0036992 A1 | 2/2011 | Fukumoto et al. |
| 2015/0077617 A1 | 3/2015 | Komiya et al. |

FOREIGN PATENT DOCUMENTS

| JP | 2007-171214 A | 7/2007 |
| JP | 2011-059095 A | 3/2011 |
| WO | 96/23213 A1 | 8/1996 |
| WO | 03/077263 A2 | 9/2003 |
| WO | 2013/190938 A1 | 12/2013 |

OTHER PUBLICATIONS

International Search Report of PCT/JP2015/052933 dated Apr. 28, 2015.

* cited by examiner

LIGHT EMITTING POINT ARRAY DIRECTION (a)

(b)

(c)

MULTICOLOR DETECTION DEVICE

TECHNICAL FIELD

The present invention relates to a multicolor detection system which irradiates a plurality of channels provided inside a plurality of capillaries or a microchip with light such as a laser beam and detects fluorescence, phosphorescence, scattered light, or the like emitted by a substance present inside the capillary or the channel with high sensitivity.

BACKGROUND ART

A capillary array DNA sequencer which collectively deciphers base sequences of different DNA samples in individual capillaries by performing electrophoretic analysis with in parallel processing using the plurality of capillaries (glass capillary each having an outer diameter of 100 μm to 400 μm and inner diameter of 25 μm to 100 μm) filled with a separation medium is widely used. This mechanism will be described later. A polyimide coating film is formed on an outer surface of a commercial capillary in order to preserve flexibility. A portion where an electrophoretic length of each capillary is constant, for example, a portion near a position of 30 cm distance away from a sample injection end of the capillary is arranged to be aligned on the same plane in a state where the coating film is removed and a laser beam is irradiated from a side of a capillary-array plane so as to simultaneously irradiate the plurality of capillaries with the laser beam. Hereafter, the capillary-array plane may be simply called a array plane in the present specification. A fluorescent labeled DNA, which is subjected to electrophoresis, inside each capillary described above emits fluorescence by being excited by laser irradiation when the DNA is passed across the laser beam. Here, DNA is labeled with fluorescent substances of four colors depending on the terminal base species of A, C, G, and T. As a result, laser-irradiation positions of respective capillaries become light-emitting points and a plurality of light-emitting points are arranged on a straight line at intervals of p. Hereafter, this is called a light-emitting-point array. When the number of the light-emitting points (number of capillaries) is set to n, the entire width W of the light-emitting-point array is $W=p*(n-1)$. For example, when $p=0.36$ mm and $n=24$, $W=8.28$ mm. A fluorescence-detection system collectively detects respective light beams emitted from the light-emitting-point array while spectroscopically separating the light beams. A configuration of the system is illustrated in FIG. 3 of PTL 1.

First, respective emitted light beams are turned into parallel-light beams by a common condensing lens. Hereafter, an expression of "common" is used as the meaning (n-to-1 correspondence) that one optical element is used for a plurality of light-emitting points (n light-emitting points). In contrast, an expression of "individual" is used as the meaning (1-to-1 correspondence) that one optical element is used for one light-emitting point. Here, when a focal length of the common condensing lens is set as f and an effective diameter is set as D1, $W<f$ and $W<D1$. For example, $f=50$ mm and $D1=36$ mm. Next, the parallel-light beams are allowed to be passed through a long pass filter so as to cut a wavelength of the laser beam and further allowed to be transmitted through a common transmission type diffraction grating so as to be subjected to wavelength dispersion in the long axis direction of each capillary, that is, the direction orthogonal to both the array direction of the light-emitting-point array and the optical axis of the common condensing lens. Here, when the effective diameter of the common transmission type diffraction grating is set as DG, it needs to be $D1 \leq DG$ so as not to decrease detection efficiency. For example, $DG=50$ mm. Subsequently, the image of respective parallel-light beams formed on the two-dimensional sensor by the common imaging lens. Here, when the effective diameter of the common imaging lens is set as D2, it needs to be $D1 \leq D2$ so as not to decrease detection efficiency. For example, $D2=36$ mm. With matters as described above, it is possible to collectively acquire wavelength dispersion spectra of respective light beams emitted from the light-emitting-point array. Finally, temporal change in respective wavelength dispersion spectra is analyzed so as to obtain temporal change in intensity of fluorescence of four colors and determine the sequence of base species, that is, the base sequence.

Other means for simultaneously detect fluorescence of four colors is illustrated in FIG. 2 of NPL 1. First, light beam emitted from one light-emitting area is turned into parallel-light beam by one condensing lens (here, objective lens). Here, when the entire width of the light-emitting area is set as W, the focal length of the objective lens is set as f, and the effective diameter is set as D1, $W<f$ and $W<D1$. The objective lens in use is UPLSAP0 60X W which is the Olympus's product, and $W=0.44$ mm, $f=3$ mm, and $D1=20$ mm. Next, the parallel-light beam is divided into four parallel-light beams of four colors by one set of three kinds of dichroic-mirrors. Subsequently, images of respective parallel-light beams are formed on four two-dimensional sensors by one set of four imaging lenses. Here, when the effective diameter of each imaging lens is set as D2, it needs to be $D1<D2$ so as not to decrease detection efficiency. With matters as described above, it is possible to collectively acquire four-divided images of four colors of the light-emitting area.

On the other hand, other means for simultaneously detect light beams emitted from the light-emitting-point array is illustrated in FIG. 1 of PTL 2. First, respective light beams emitted from the light-emitting-point array are turned into the parallel-light beams by an individual condensing-lens array. Here, when intervals between the light-emitting points is set as p and the number of light-emitting points is set as n, the entire width of the light-emitting-point array is $W=p*(n-1)$, and when the effective diameter of each condensing lens is set as D1, $D1<W$. It is set that $D1<p$ to thereby make it possible to set an individual condensing-lens array in which respective condensing lenses are aligned in a straight line. Next, respective parallel-light beams are made incident on respective individual sensors of the individual sensor array. With matters as described above, it is possible to collectively acquire intensities of light beams emitted from the light-emitting-point array.

CITATION LIST

Patent Literature

PTL 1: JP 2007-171214 A
PTL 2: JP 2011-59095 A

Non Patent Literature

NPL 1: Rev Sci Instrum., 2011 February; 82(2):023701.

SUMMARY OF INVENTION

Technical Problem

The fluorescence-detection system of PTL 1 has high light condensing efficiency (light condensing efficiency by the common condensing lens) and high detection efficiency (total utilization efficiency of emitted light contributing to fluorescence-detection by the sensor based on light condensing efficiency, transmissivity of the long pass filter, diffraction efficiency of the diffraction grating, or the like) of light beams emitted from the light-emitting points and also has high spectroscopic accuracy by the diffraction grating. However, the fluorescence-detection system of PTL 1 includes two common lenses (using camera lenses) and has a relationship in which W<f and W<D1≤D2 and thus, when W is set to be constant, there is a problem to be solved that the entire size of the system is very large and manufacturing cost of the system is high. For example, in a case where f=50 mm, D1=36 mm, and D2=36 mm, the entire size of the fluorescence-detection system becomes larger than the volume of a column ($1.6 \times 10^6$ mm$^3$) having the diameter of 100 mm and the height of 200 mm. In the present specification, an entire size of a fluorescence-detection system is represented by an occupation volume of an optical system spanning from a light-emitting point to an image-forming point and an occupation volume of a sensor itself is not included in representation of the entire size. Setting of W<<f and W<<D1 cannot be allowed (huge camera lens is needed to achieve the setting) and thus, there is a problem to be solved that detection efficiency of the end light-emitting point (the light-emitting point positioned in the vicinity of the ends of the light-emitting-point array) separated from the optical axis is decreased compared to detection efficiency of the center light-emitting point (the light-emitting point positioned in the vicinity of the center of the light-emitting-point array) in the vicinity of the optical axis and variation in detection sensitivity occurs at each light-emitting point.

However, matters for solving the problems to be solved, that is, matters for realizing miniaturization and cost reduction of a system that, detects light beams of four colors emitted from a light-emitting-point array while simultaneously identifying the colors of the emitted-light beams, and reducing variation in detection sensitivity of the respective emitted-light beams have not been performed so far. When the fluorescence-detection system is miniaturized, the capillary array DNA sequencer may be installed at a small area or may be carried, or usability is improved. Also, the number of components of the fluorescence-detection system is reduced or the size of each component becomes smaller to thereby reduce manufacturing cost. Furthermore, variation in detection sensitivity of the respective light-emitting points is reduced to thereby make it possible to allow quantitive comparison of samples analyzed in the respective capillaries and improve a dynamic range and total detection sensitivity of the light-emitting-point array. As the results, the capillary array DNA sequencer can be further spread and more contribute to the world.

It is possible to perform simultaneous fluorescence-detection of light beams of four colors emitted from a similar light-emitting-point array using the fluorescence-detection system described in NPL 1. However, since W=0.44 mm in the objective lens used in NPL 1, for example, only a portion of the entire width W=8.28 mm of the light-emitting-point array can be detected. Similar to the capillary array DNA sequencer, the common condensing lens and four common imaging lenses are used, instead of the objective lens and four individual imaging lenses. In this case, when the effective diameter of three kinds of dichroic-mirrors is set as DM, the dichroic-mirrors are disposed while being inclined at 45° relative to the parallel-light beams and thus, it needs to be $\sqrt{2} \times D1 \leq DM$ so as not to reduce detection efficiency. For example, DM=71 mm. Accordingly, even when four cameras are not included, the entire size of the fluorescence-detection system becomes larger than the case of PTL 1 and manufacturing cost is increased that much. In addition to this, space occupied by four cameras is large and cost for that is very high. Also, the problem to be solved of sensitivity variation of each light-emitting point remains as it is.

On the other hand, although when the fluorescence-detection system described in PTL 2 is used, it is possible to make the entire size of the fluorescence-detection system smaller because D1<W, there is a problem to be solved that the system corresponds to only fluorescence-detection of one color. According to PTL 1, an act of being combined with wavelength dispersion by the diffraction grating is considered. Light beams emitted from n-light-emitting points are turned into parallel-light beams by n-individual-condensing lenses, are allowed to be transmitted through n-individual-transmission-type diffraction gratings to disperse wavelengths of light beams, and the images of light beams are formed on n-one-dimensional- or n-two-dimensional-individual sensors by n-individual-imaging lenses. That is, it is a configuration in which the fluorescence-detection system of PTL 1 is miniaturized and n of such fluorescence-detection systems are aligned in parallel. Here, since D1<p and p=0.36 mm, it may be set that, for example, D1=0.3 mm. The effective diameter DG of the transmission-type diffraction grating needs to be D1≤DG and simultaneously, DG<p so as not to receive interference with an adjacent diffraction grating and it may be set that, for example, DG=0.3 mm. Although miniaturization can be allowed for the fluorescence-detection system described above compared to the case of PTL 1, it is difficult to respectively manufacture fine optical components by n components and arrange respective fine optical components at predetermined positions, and manufacturing cost is increased that much. Manufacturing of the transmission-type diffraction grating having DG=0.3 mm itself is difficult.

Next, according to NPL 1, an act of being combined with three kinds of dichroic-mirrors is considered. Light beams emitted from n-light-emitting points are turned into parallel-light beams by n-individual-condensing lenses, n-parallel-light beams are turned into n sets of four-divided-parallel-light beams of four colors using n sets each of which is formed of three kinds of individual dichroic-mirrors, and n sets of images of the four-divided parallel-light beams are formed on n sets each of which is formed of four-individual sensors by n sets of four-individual-imaging lenses. That is, it is a configuration in which the fluorescence-detection system of NPL 1 is miniaturized and n sets of the fluorescence-detection systems are aligned in parallel. Here, since D1<p and p=0.36 mm, it is set that, for example, D1=0.25 mm. The effective diameter DM of each dichroic-mirror needs to be $\sqrt{2} \times D1 \leq DM$ and simultaneously, DM<p so as not to receive interference with an adjacent dichroic-mirror, and it may be set that, for example, DM=0.35 mm. Although in the fluorescence-detection system described above, variation of detection sensitivity of the light-emitting points is reduced compared to the case of PTL 1, it is difficult to manufacture fine optical components by n components or n sets of components and arrange respective fine optical components at predetermined positions, and manufacturing cost is increased that much. Arranging of n sets of the four-divided images while avoiding interference itself is difficult. Furthermore, manufacturing of the dichroic-mirror having DM=0.35 mm itself is difficult.

In the matters described above, although description was made on fluorescence-detection of four colors on the assumption that it is applied to the fluorescence-detection system of the capillary array DNA sequencer, solving the problem to be solved is not limited to the capillary or fluorescence-detection of four colors, but is commonly applied to detection of emitted lights of multicolor of two or more colors regarding light beams emitted from an arbitrary light-emitting-point array.

Solution to Problem

A multicolor detection system according to the present invention includes a condensing-lens array in which a plurality of condensing lenses, that turn lights emitted from respective light-emitting points of a light-emitting-point array in which a plurality of light-emitting points are arranged, individually into parallel-light beams, respectively are arranged, at least one spectroscopic element on which the parallel-light beams are incident in parallel and which is being common, and at least one common sensor on which light beams spectroscopically separated by the spectroscopic element are incident in parallel.

As the spectroscopic element, a diffraction grating, a prism, or a dichroic-mirror may be used.

A multicolor detection system according to the present invention includes the condensing-lens array in which a plurality of condensing lenses, that turn lights emitted from respective light-emitting points of a light-emitting-point array in which a plurality of light-emitting points are arranged, individually into parallel-light beams, respectively, are arranged and at least one common color sensor on which the parallel-light beams are incident in parallel.

A multicolor detection system according to the present invention includes the condensing-lens array in which a plurality of condensing lenses, that turn lights emitted from respective light-emitting points of a light-emitting-point array in which a plurality of light-emitting points are arranged, individually into parallel-light beams, respectively, are arranged and at least one common sensor on which the parallel-light beams are incident in parallel, and when an average effective diameter of the light-emitting points is set as d, an average focal length of the condensing lenses is set as f, an average effective diameter of the condensing lenses is set as D, and an average optical distance between the condensing lenses and the sensor is set as g, the multicolor detection system satisfies $f \leq -0.20*(d/D)*g+2.8*D.$ A multicolor detection system according to the present invention includes the condensing-lens array in which a plurality of condensing lenses, that turn lights emitted from respective light-emitting points of a light-emitting-point array in which a plurality of light-emitting points are arranged, individually into parallel-light beams, respectively, are arranged and at least one common sensor on which the parallel-light beams are incident in parallel, and when an average effective diameter of the light-emitting points is set as d, an average array interval of the light-emitting points is set as p, and an average optical distance between the condensing lenses and the sensor is set as g, the multicolor detection system satisfies $f \geq 0.95*(d/p)*g.$ A multicolor detection system according to the present invention includes the condensing-lens array in which a plurality of condensing lenses, that turn lights emitted from respective light-emitting points of a light-emitting-point array in which a plurality of light-emitting points are arranged, individually into parallel-light beams, respectively are arranged, and an imaging-lens array on which a plurality of imaging lenses, each of which turns the parallel-light beams individually into condensed-light beams, are arranged, and at least common one sensor on which the condensed light beams are incident in parallel, and when an average effective diameter of the light-emitting points is set as d, an average focal length of the condensing lenses is set as f, an average effective diameter of the condensing lenses is set as D, and an average optical distance between the condensing lenses and the corresponding imaging lenses is set as g, the multicolor detection system satisfies $f \leq -0.20*(d/D)*g+2.8*D$ A multicolor detection system according to the present invention includes the condensing-lens array in which a plurality of condensing lenses, that turn lights emitted from respective light-emitting points of a light-emitting-point array in which a plurality of light-emitting points are arranged, individually into parallel-light beams, respectively, are arranged, an imaging-lens array on which a plurality of imaging lenses, each of which turns the parallel-light beams individually into condensed light beams, respectively, are arranged, and at least one common sensor on which the condensed light beams are incident in parallel, and when an average effective diameter of the light-emitting points is set as d, an average array interval of the light-emitting points is set as p, an average focal length of the condensing lenses is set as f, and an average optical distance between the condensing lenses and the corresponding imaging lenses is set as g, the multicolor detection system satisfies $f \geq 0.95*(d/p)*g$ The device according to the present invention is a device integrated with a channel array on which at least part of a plurality of channels are arranged on the same plane and a condensing-lens array on which condensing lenses, each of which turns light emitted from each channel of the channel array individually into parallel-light beam, are arranged.

The plurality of channels may be present inside the plurality of capillaries and may be formed inside a microchip.

Advantageous Effects of Invention

According to the present invention, it is possible to miniaturize a system which performs multicolor detection of light beams emitted from the light-emitting-point array and to miniaturize the entire size of various apparatuses using the system. Accordingly, it is possible to reduce space in which the system or the apparatuses is to be placed, the system or the apparatuses can be carried, and usability of the system or the apparatuses is improved. The number of components constituting the system is reduced and the component itself is miniaturized to thereby make it possible to reduce manufacturing cost.

In addition to matters described above, a problem to be solved, a configuration, and effect will be apparent from description of the following embodiments.

DESCRIPTION OF EMBODIMENTS

Figure 1:
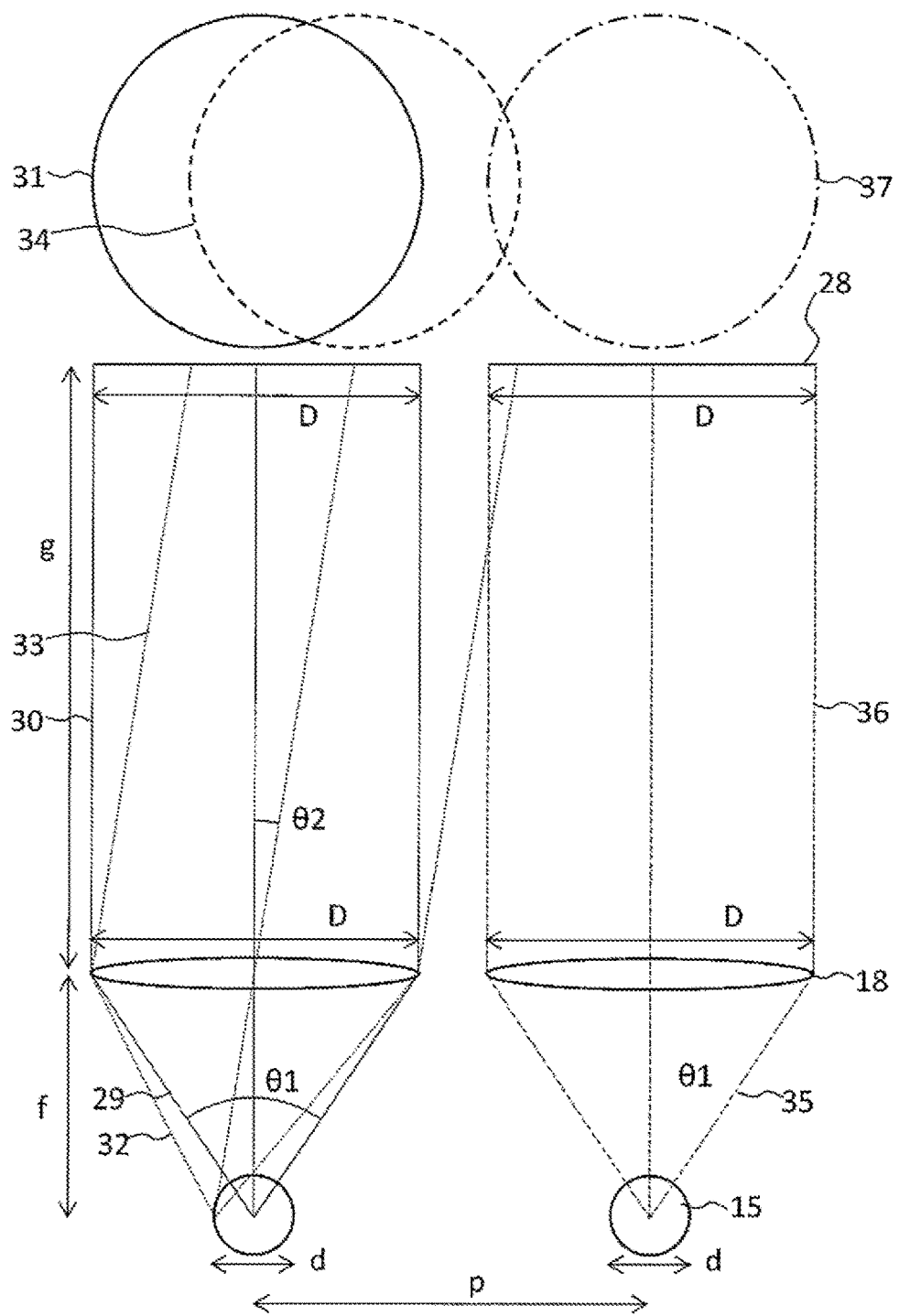
FIG. 1 is a schematic diagram of a configuration example of a fluorescence-detection system in which respective light beams emitted from a light-emitting-point array are respectively turned into parallel-light beams by individual condensing lenses and are made incident on a sensor area to be detected.

The present invention provides means for realizing miniaturization and cost reduction of a system that, detects light beams of four colors emitted from a light-emitting-point array while simultaneously identifying the colors of the light beams, and reducing variation in detection sensitivity of the respective emitted light beams. Firstly, the present invention will be overviewed.

First, the respective light beams emitted from the light-emitting-point array are turned into parallel-light beams by an individual condensing-lens array. Although an expression of a parallel-light beam is frequently used, it does not necessarily mean a light beam of which constitutional light-elements are parallel to each other in the strict sense, but it means a light beam in which angles between light-elements are made smaller and comes close to zero by the condensing lens compared with those in the light beam that is not condensed by the condensing lens. Here, when an average interval of the light-emitting points is set as p and the number of the light-emitting points and the number of individual condensing lenses are respectively set as n, the entire width of the light-emitting-point array is $W=p*(n-1)$. When an average focal length of the condensing lenses is set as f and an average effective diameter of the condensing lenses is set as D1, $D1<W$. It is set that $D1<p$ to thereby make it possible to set an individual condensing-lens array in which respective condensing lenses are aligned in a straight line. For $p=0.36$ mm, $n=24$, and $W=8.28$ mm, it is set that, for example, $f=1$ mm and $D1=0.3$ mm.

Next, each parallel-light beam is transmitted through a spectroscopic element, for example, one common transmission-type diffraction grating, to be subjected to wavelength dispersion. Here, when an effective diameter of the transmission-type diffraction grating in an array direction of the light-emitting-point array is set as DG1 and an effective diameter of the transmission-type diffraction grating in along axis direction of each capillary is set as DG2, it is set that $(W+D1) \leq DG1$ and $D1 \leq DG2$ so as not to decrease detection efficiency. It may be set that, for example, $DG1=10$ mm and $DG2=1$ mm. In this case, 24-parallel-light beams separated from each other are incident on different points of the one-common transmission-type diffraction grating and are respectively subjected to wavelength dispersion in parallel. A diameter of each parallel-light beam is about $D1=0.3$ mm and the diameter is sufficiently large compared to a grating constant of the diffraction grating and thus, all of the parallel-light beams can be subjected satisfactorily to wavelength dispersion. The direction of wavelength dispersion is set to the long axis direction of each capillary, that is, a direction perpendicular to the array direction of the light-emitting-point array and the optical axis of each condensing lens.

Subsequently, images of the parallel-light beams subjected to wavelength dispersion are formed on one common two-dimensional sensor by n-individual-imaging lenses. For an average effective diameter D2 of the imaging lenses, it needs to be $D1 \leq D2$ so as not to decrease detection efficiency. For example, $D2=0.3$ mm. With matters as described above, it is possible to collectively perform fluorescence-detection of four colors of the light beams emitted from the light-emitting-point array.

According to the fluorescence-detection system described above, a size of the system is miniaturized compared to the case of PTL 1 and also the diffraction grating and the sensor are used in common for a plurality of light-emitting points and accordingly, a configuration of the system is simplified and mounting becomes easy. The entire size of the fluorescence-detection system becomes smaller than a column having the diameter of 10 mm and the height of 20 mm. Although the diffraction grating and the sensor are used in common, the fluorescence-detection optical system and detection efficiency for each light-emitting point are equivalent, it is possible to reduce sensitivity variation. Even when the transmission-type diffraction grating is replaced with a wavelength dispersion prism, similarly, it is possible to solve the problem to be solved by the matters described above.

Another aspect of the present invention will be described. First, respective light beams emitted from a light-emitting-point array are turned into parallel-light beams by an individual condensing-lens array. Here, when an average interval of the light-emitting points is set as p and the number of the light-emitting points and the number of individual condensing lenses are respectively set as n, the entire width of the light-emitting-point array is $W=p*(n-1)$. When an average focal length of the condensing lenses is set as f and an average effective diameter of the condensing-lenses is set as D1, $D1<W$. It is set that $D1<p$ to thereby make it possible to set an individual condensing-lens array in which the respective condensing lenses are aligned in a straight line. For P-0.36 mm, n-24, and W-8.28 mm, it is set that, for example, $f=1$ mm and $D1=0.3$ mm.

Next, the respective parallel-light beams are turned into n sets of four-divided parallel-light beams of four colors by arranging one set of three kinds of common dichroic-mirrors and one total reflection mirror in parallel to the long axis direction of each capillary, that is, a direction orthogonal to both of an array direction of the light-emitting-point array and the optical axis of each condensing lens and the parallel-light beams propagate in a direction perpendicular to an array plane of the capillary array, that is, a direction parallel to the optical axis of each condensing lens. When an average effective diameter of the dichroic-mirrors and the total reflection mirror in the array direction of the light-emitting-point array is set as DM1 and an average effective diameter thereof in a direction orthogonal to the array direction is set as DM2, it is set that $(W+D1) \leq DM1$ and $\sqrt{2} \times D1 \leq DM2$ so as not to decrease detection efficiency. It may be set that, for example, $DM1=10$ mm and $DM2=1$ mm. In this case, the 24 parallel-light beams separated from each other are incident on different points of each of three kinds of common dichroic-mirrors and are respectively divided into two light beams of transmitted light and reflected light. Uniform performance is obtained on any point of any of the dichroic-mirrors and thus, all of the parallel-light beams can be spectroscopically separated satisfactorily. The total reflection mirror may be replaced with the dichroic-mirror.

Subsequently, n sets of the four-divided parallel-light beams of four colors are incident on one common two-dimensional sensor without being focused by imaging lenses. In a case where the parallel-light beam is spectroscopically separated by wavelength dispersion with use of the diffraction grating or the prism, as described above as, when the images of the parallel-light beams subjected to wavelength dispersion are not formed by the imaging lens(es), a desired spectroscopic accuracy is not obtained. In contrast, in a case where the parallel-light beams are spectroscopically separated by the dichroic-mirrors, since it not necessary to form images of the parallel-light beams, the imaging lens(es) can be omitted. With matters as described above, it is possible to collectively perform fluorescence-detection of four colors of light beams emitted from the light-emitting-point array.

According to the fluorescence-detection system described above, a size of the system is miniaturized compared to the case of PTL 1 and also the dichroic-mirrors, the total reflection mirror, and the sensor are used in common for a plurality of light-emitting points and accordingly, a configuration of the system is simplified and mounting becomes easy. The entire size of the fluorescence-detection system becomes smaller than a column having the diameter of 10 mm and the height of 10 mm. Although the dichroic-mirrors and the sensor are used in common, the fluorescence-detection optical system and detection efficiency for each light-emitting point are equivalent and it is possible to reduce variation in sensitivity.

Another aspect of the present invention will be described. First, respective light beams emitted from a light-emitting-point array are turned into parallel-light beams by an individual condensing-lens array. Here, when an average interval of the light-emitting points is set asp and the number of the light-emitting points and the number of the condensing lenses are respectively set as n, the entire width of the light-emitting-point array is $W=p*(n-1)$. When an average focal length of the condensing-lenses is set as f and an average effective diameter of the condensing lenses is set as D1, $D1<W$. It is set that $D1<p$ to thereby make it possible to set an individual condensing-lens array in which the respective condensing lenses are aligned in a straight line. For $P=0.36$ mm, $n=24$, and $W=8.28$ mm, it is set that, for example, $f=1$ mm and $D1=0.35$ mm.

Subsequently, the respective parallel-light beams are incident on one common single-plate two-dimensional color sensor without being focused by imaging lenses. In the color sensor, at least four kinds of pixels, that respectively identify four colors, are respectively arranged on a two-dimensional sensor surface in a multitude, or the color sensor is for identifying four colors by one kind of pixels, which are arranged in a multitude, in a direction (propagation direction of incident light) perpendicular to the two-dimensional sensor surface. Here, when an average diameter of the pixels is set as S, it needs to be $S<D1$. An average diameter of the parallel-light beams is $D1=0.35$ mm. In contrast, when the sensor in which four kinds of pixels identifying four colors are arranged is used and it is set that $S=0.05$ mm, each parallel-light beam is detected by approximately 40 pixels on the color sensor. In this case, each parallel-light beam is detected by 10 pixels per one kind of pixel identifying one color and thus, it possible to reduce variation in sensitivities of the four colors and allow high-accuracy spectroscopy by accumulating intensities of the pixels for each color.

In contrast, when it is assumed that the images of the respective parallel-light beams are formed by an individual imaging-lens array, and for example, a spot diameter of the formed images is 0.05 mm, each image is detected only by approximately one pixel on the color sensor and therefore favorable spectroscopy becomes impossible. That is, in this state, no use of the imaging lenses contributes to miniaturization of the system and also improvement of spectroscopic accuracy. With matters as described above, it is possible to collectively perform fluorescence-detection of four colors of light beams emitted from the light-emitting-point array.

According to the fluorescence-detection system described above, a size of the system is miniaturized compared to the case of PTL 1 and also a configuration of the system is very simple. The entire size of the fluorescence-detection system becomes smaller than a column having the diameter of 10 mm and the height of 5 mm. The fluorescence-detection optical system and detection efficiency for each light-emitting point are equivalent and it is possible to reduce sensitivity variation.

In the matters described above, although description was made on fluorescence-detection of four colors on the assumption that it is applied to the fluorescence-detection system of the capillary array DNA sequencer, means for solving the problem to be solved is not limited to the capillary or fluorescence-detection of four colors, but is commonly applied to detection of emitted lights of multicolor of two or more colors regarding light beams emitted from an arbitrary light-emitting-point array.

In the following, description will be made in detail with reference to the drawings.

Although a size of each light-emitting point of a light-emitting-point array targeted by the present invention is small, the size is finite, and cannot be ignored when miniaturizing a fluorescence-detection system. FIG. 1 is a schematic diagram of a configuration example of a fluorescence-detection system in which respective light beams emitted from a light-emitting points are respectively turned into parallel-light beams by individual condensing lenses and are made incident on a sensor area to detect the parallel-light beams. FIG. 1 illustrates a configuration in which light emitted from the light-emitting point 15 having an average effective diameter d is turned into a parallel-light beam by an individual condensing lens 18 having an average focal length f and an average effective diameter D and is made incident on a sensor area 28 located at a position an average distance g away from the individual condensing lens 18 and having an average effective diameter D to be detected. The average effective diameter D of the sensor area 28 does not necessarily indicate the entire size of the sensor and may be regarded as an area allocated for detection of the light-emitting point 15 by a portion of a sensor having a larger size. In a case of a fluorescence-detection system which is not illustrated in FIG. 1 and which re-condenses or forms images of the respective parallel-light beams by individual imaging lenses, makes the re-condensed beams or the images incident on a sensor area, and detects the re-condensed beams or the images, in the following discussion, an average distance g between a sensor area 28 and an individual condensing lens 18 is replaced with an average distance g between an individual imaging lens and an individual condensing lens 18.

Firstly, attention will be paid to the light-emitting point 15 in the left side of FIG. 1. The light beam 29 emitted from the center of the light-emitting point 15 is turned into the parallel-light beam 30 by the condensing lens 18, forms a spot 31 on the sensor area 28, and the sensor area 28 coincides with the spot 31. In this case, when D is set to be constant, the smaller f gives the more detection-light quantity together with a light-receiving angle $\theta 1$. More accurately, when $F=f/D$, the detection-light quantity is increased in proportion to $1/F^2$. On the other hand, a spot 34 of the parallel-light beam 33 of the light beam 32 emitted from the left end of the light-emitting point 15 is shifted from the sensor area 28 to the right. That is, the spot 31 is wholly detected, but the spot 34 is detected with a portion amounting to an overlap ratio between the spots 31 and 34. The greater the overlap, the detection-light quantity over the entire area of the light-emitting point is increased. To do this, it is desirable to set an angle $\theta 2$ between the optical axis of the parallel-light beam 30 and the optical axis of the parallel-light beam 33 to be small. When d is set to be constant, the larger f gives the smaller $\theta 2$ and thereby the more detection-light quantity. As described above, in order to increase the detection-light quantity of the light-emitting point 15, although there is a trade-off relationship between a side in which the f is desirably made small and a side in which the f is desirably made large, investigation about what f is the best had not been performed so far. Next, conditions of the f and g for increasing the detection-light quantity of the light-emitting point 15 will be clarified.

Figure 3:
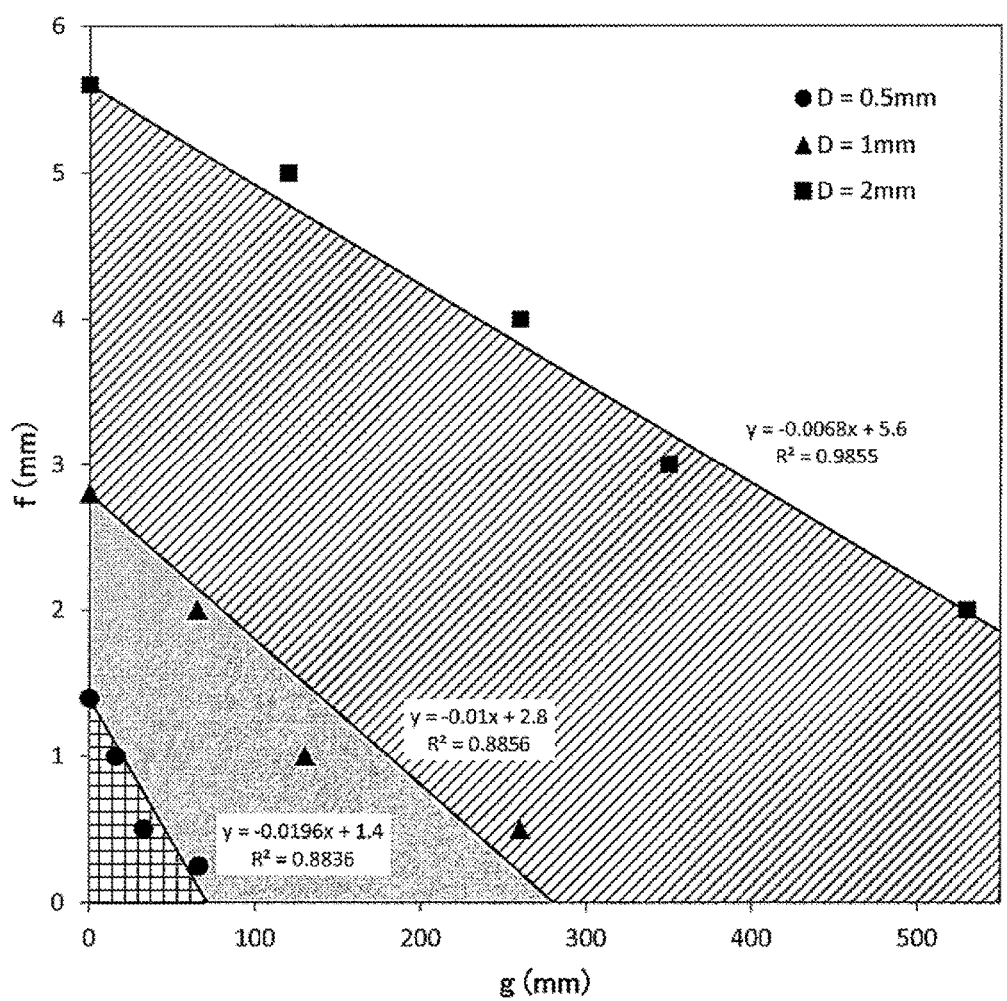
FIG. 3 is a diagram illustrating a relationship between g and f, at which the relative detected-light quantity becomes 50% or more, by using D as a parameter.

In order to evaluate the detection-light quantity, the fluorescence-detection system illustrated in FIG. 3 of PTL 1 is used as a reference. In a typical example of the fluorescence-detection system, a focal length of a common condensing lens is f=50 mm and an effective diameter D1 is D1≥25 mm. F-number of the lens is $F=f/D1 \leq 2.0$. In a case where a condensing lens having $F_0=2.0$ is used, when light emitted from a light-emitting point having an infinitely small size and positioned at a focal point of the lens is turned into a parallel-light beam by the lens and the parallel-light beam is detected by the sensor without loss, a detected-light quantity at that time is set as a reference (100%). Hereafter, a detected-light quantity for an arbitrary light-emitting point having an infinitely small size is evaluated by a relative detected-light quantity with respect to the reference. It is considered that the light-emitting point having a finite size with the average effective diameter d is composed of a multitude of light-emitting points each having an infinitely small size. In the present specification, the "light-emitting point having a finite size" is simply called a "light-emitting point" and the "light-emitting point having an infinitely small size" is called a "light-emitting point having an infinitely small size" at all such times. The relative detected-light quantity of the light-emitting point is set as an average of the relative detected-light quantity of a large number of light-emitting points having an infinitely small size and constituting the light-emitting point. For example, in the example described above, when the condensing lens is replaced with a condensing lens of F=1.4, light-condensing efficiency is increased $(F_0/F)^2=2.0$ times and thus, the relative detected-light quantity of the light-emitting point having an infinitely small size and positioned at the focal point of the lens becomes 200%. Here, it is assumed that the entire light quantity omni-directionally emitted from the light-emitting point is constant and light-emitting density within the inside the light-emitting point is spatially uniform. In the typical example of the present fluorescence-detection system, the interval between the light-emitting points of the light-emitting-point array is p=0.36 mm, the number of the light-emitting points is n=24, the entire width of the light-emitting-point array is $W=p*(n-1)=8.28$ mm. Since the light-emitting point at the center of the light-emitting-point array is positioned at vicinity of the focal point of the lens, the relative detected-light quantity of the light-emitting point is almost 100%. On the other hand, since the light-emitting point at either end of the light-emitting-point array is positioned away from the focal point of the lens, the relative detected-light quantity of the light-emitting point is decreased to become approximately 50%. The present invention aims to make the relative detected-light quantity of each light-emitting point 50% or more so that multicolor detection sensitivity of each light-emitting point becomes greater than or equal to that in the related art.

Figure 2:
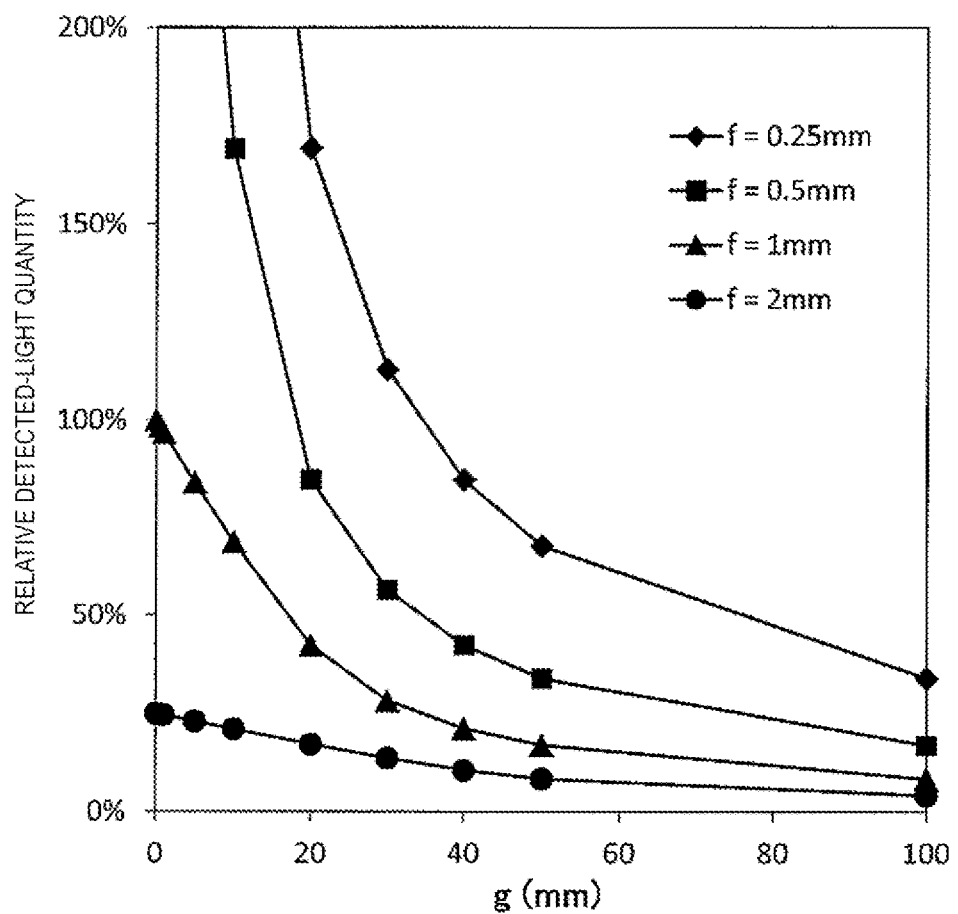
FIG. 2 is a diagram illustrating a relationship between g and a relative detected-light quantity, by using f as a parameter.

FIG. 2 is a diagram illustrating a relationship between g and a relative detected-light quantity, by using f as a parameter in the configuration illustrated in FIG. 1. Here, the average effective diameter of the light-emitting point 15 was set as d=0.05 mm. The average effective diameter of the individual condensing lens 18 was set as D=0.5 mm. The relative detected-light quantity was calculated based on F-number, F=f/0.05 of the lens. The light-emitting point 15 having the effective diameter d=0.0 mm is composed of approximately 500 light-emitting points having an infinitely small size and arranged at 0.1 µm intervals, and the relative detected-light quantity is calculated for each light-emitting point having the infinitely small size, based on the same calculation of overlap area ratio of the spot 31 and the spot 34 of FIG. 1. The relative detected-light quantity of the light-emitting point 15 is obtained by averaging the relative detected-light quantities of all the light-emitting points having the infinitely small size. As a result, it was firstly found out that the smaller the f and the smaller the g, the greater the relative detected-light quantity. This indicates that effect of increase of the relative detected-light quantity of the light-emitting point having the infinitely small size and positioned at the center of the light-emitting point 15 caused by making the f small (making F small and making θ1 large) is greater than effect of increase of the overlap area ratio (increase of the relative detected-light quantity of the light-emitting point having the infinitely small size and positioned at the end of the light-emitting point 15) caused by making the f large (making θ2 small). Also, it indicates that effect of increase of the overlap area ratio by making g small is large for an arbitrary f.

FIG. 3 is a graph having the lateral axis g and the vertical axis f and illustrating a relationship between g and f, in which the condition that the relative detected-light quantity is 50% or more is satisfied, based on the calculation results of FIG. 2. Here, D is used as a parameter. It was found out that if g and f fall within an area located lower than a straight line having negative inclination, the relative detected-light quantity becomes 50% or more, whatever the value of the D may be. The greater the D, the greater the vertical axis-intercept of the boundary straight line, the smaller the inclination and thus, an area satisfying the condition became large. As a result of analysis made in detail, it was found out that in general, the area satisfying the condition is represented as, $$f \leq -0.20*(d/D)*g + 2.8*D \quad (1)$$

Similar to the results of FIG. 2, the smaller the respective f and g, that is, as a coordinate in FIG. 3 comes close to the origin of FIG. 3, the relative detected-light quantity is increased. However, since there are actually various physical restrictions, it is desirable that suitable f and g are set within the area illustrated in FIG. 3.

On the other hand, in FIG. 1, similar to the light-emitting point 15 on the left side, a light beam 35 emitted from the center of the light-emitting point 15 on the right side is turned into a parallel-light beam 36 by the condensing lens 18, and a spot 37 of the beam coincides with the sensor area 28 so that the light beam 35 is detected without loss. However, because the spot 34 of the parallel-light beam 33 of the light beam 32 emitted from the left end of the light-emitting point 15 on the left side is shifted from the sensor area 28 to the right side, the spot 34 may overlap the sensor area 28 of the light-emitting point 15 on the right side, and it becomes crosstalk in detecting the light-emitting point 15 on the right side. The crosstalk is represented by an overlap ratio of the spot 37 and the spot 34. Here, respective parameters of d, f, D, and g are equal between the light-emitting point on the left side and the light-emitting point on the right side, an average interval between both the light-emitting points is p. Although not illustrated in FIG. 1, a spot of a parallel-light beam of the light beam emitted from the right end of a light-emitting point, which is adjacent to a right side of the light-emitting point 15 on the right side, similarly, overlaps the spot 37 and becomes crosstalk in detecting the light-emitting point 15 on the right side. In order to satisfactorily detect light beams emitted from respective light-emitting points, the smaller the crosstalk, the better, and the crosstalk should be smaller at least than signal intensity. The present invention aims to achieve detection of respective light-emitting points with low crosstalk by suppressing respective crosstalk/signal intensity ratio to be less than or equal to 25%, because crosstalk intensities from two light-emitting points adjacent to both sides of the light-emitting point of interest are equally generated.

Figure 4:
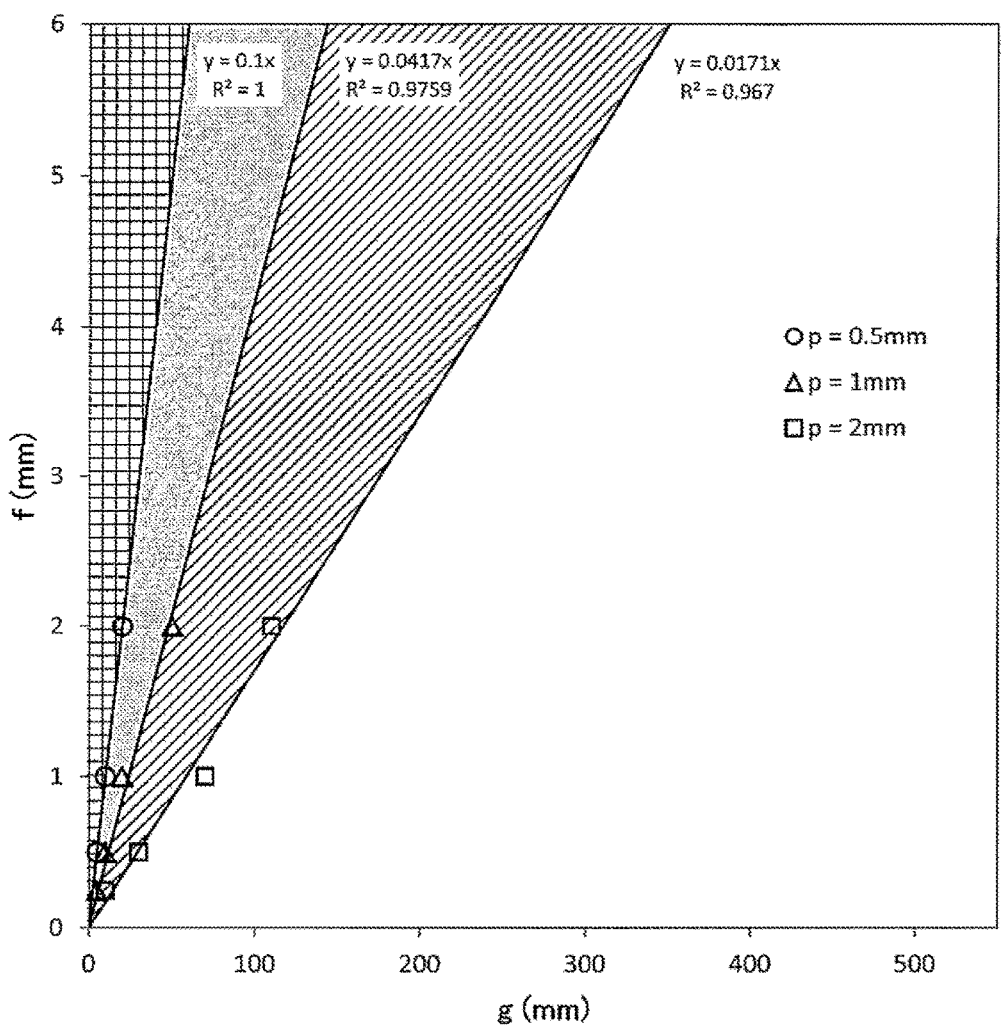
FIG. 4 is a diagram illustrating the relationship between g and f, at which a crosstalk/signal intensity ratio becomes 25% or less, by using p as a parameter.

FIG. 4 is a graph having the lateral axis g and the vertical axis f and illustrating a relationship between g and f, in which the condition that the crosstalk/signal intensity ratio is 25% or less is satisfied. Here, the average effective diameter of the light-emitting point was set as d=0.05 mm. And, p was used as the parameter and it was set that D=p. It was found out that if g and f fall within an area located upper than a straight line which passes through an origin and has a positive inclination, the crosstalk/signal intensity ratio becomes 25% or less, whatever the value of the p may be. The greater the parameter p, the smaller the inclination, and thus, an area satisfying the condition became large. As a result of analysis made in detail, it was found out that in general, the area satisfying the condition is represented as $$f \leq 0.95*(d/p)*g \quad (2)$$

Unlike the relative detected-light quantity of FIG. 3, the greater the f and the smaller the g, it is possible to suppress the crosstalk to be smaller. That is, it was found out that regarding the f, there is a trade-off relationship between a case where the relative detected-light quantity becomes large and a case where the crosstalk becomes small.

Figure 5:
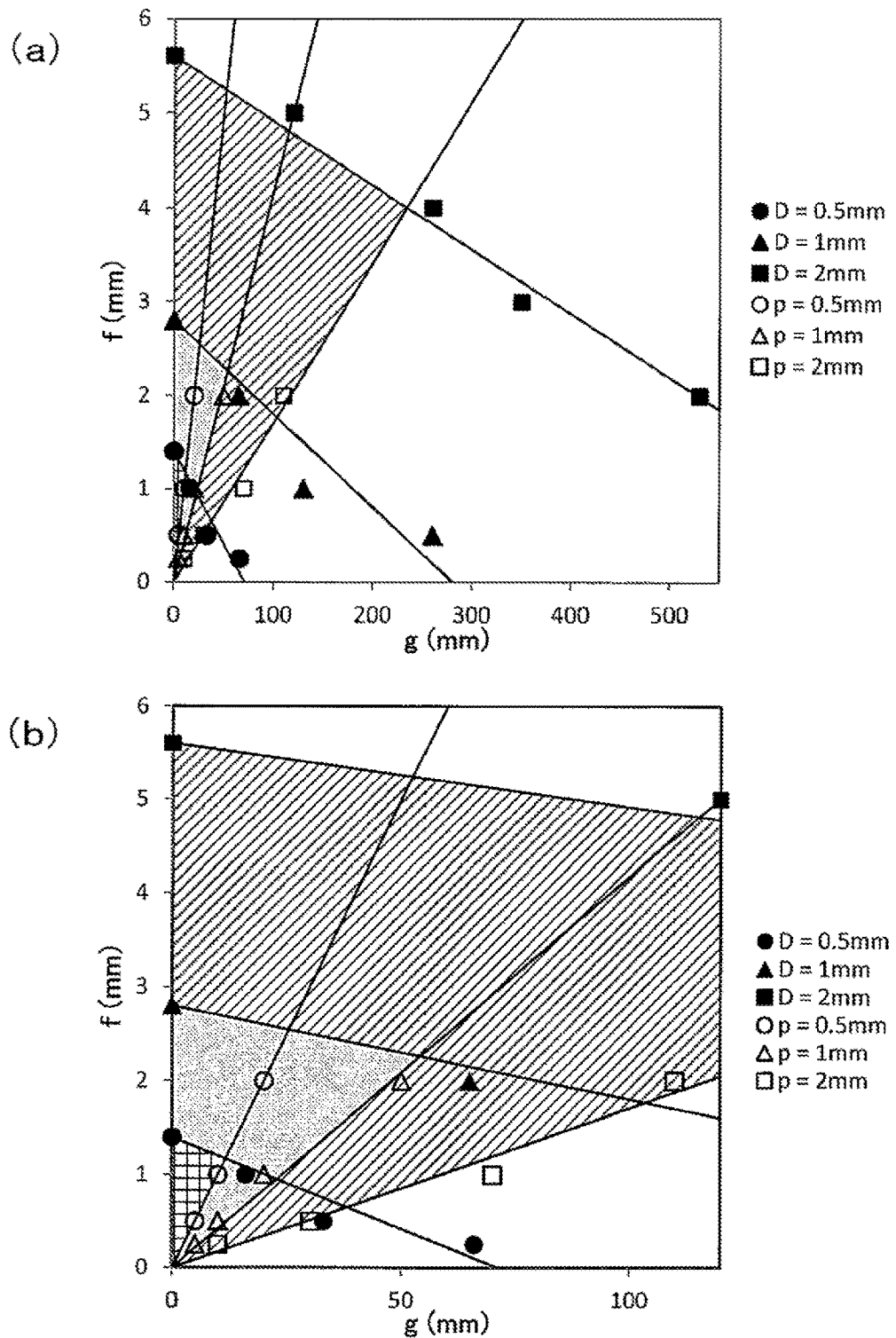
FIG. 5 is a diagram illustrating the relationship between g and f, at which the relative detected-light quantity becomes 50% or more and the crosstalk/signal intensity ratio becomes 25% or less, by using D and p as the parameters.

FIG. 5(*a*) is a graph having the lateral axis g and the vertical axis f and illustrating a relationship between g and f, in which the conditions that the relative detected-light quantity is 50% or more and the crosstalk/signal intensity ratio is 25% or less is satisfied. FIG. 5(*b*) is an enlarged view of FIG. 5(*a*). Here, the average effective diameter of the light-emitting point was d=0.05 mm and it was set that D=p. The area satisfying the conditions is an area in which the area of FIG. 3 and the area of FIG. 4 are overlapped with each other, needless to say. As the parameters D and p are increased, respectively, the area satisfying the conditions becomes large. The area satisfying the conditions, in general, can be represented by the equation (1) and the equation (2).

In the following, examples of the present invention will be described.

Example 1

Figure 6:
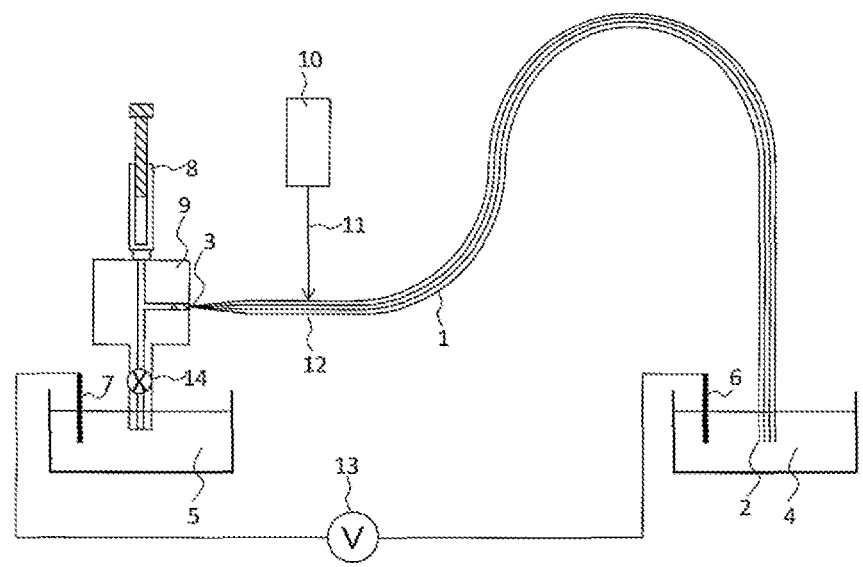
FIG. 6 is a schematic diagram illustrating a configuration example of a capillary array DNA sequencer.

FIG. 6 is a schematic diagram illustrating a configuration example of a system of a capillary array DNA sequencer. An analytical procedure will be described using FIG. 6. First, sample-injection ends 2 of a plurality of capillaries 1 (four capillaries are illustrated in FIG. 6) are immersed in a cathode-side buffer solution 4 and sample-elution ends 3 are immersed in an anode-side buffer solution 5 through a pump block 9. A valve 14 of the pump block 9 is closed, a polymer solution inside the pump block 9 is pressurized by a syringe 8 connected to the pump block 9, and insides of the respective capillaries 1 is filled with the polymer solution from the sample-elution end 3 toward the sample-injection end 2. Next, the valve 14 is open, different samples are injected from respective sample-injection ends 2 into the respective capillaries 1, and then, a high voltage is applied from a power source 13 between a cathode electrode 6 and an anode electrode 7 to thereby start capillary electrophoresis. In each capillary 1, DNAs labeled by fluorescent substances of four colors electrophoretically migrate from the sample-injection end 2 to the sample-elution end 3. A part of a coating of each capillary 1 at position (laser-irradiation position 12) where DNAs electrophoretically migrate a fixed distance from the sample-injection end 2 in each capillary 1 is removed. The laser-irradiation positions 12 of the capillaries 1 are arrayed on the same plane (array plane), and are simultaneously irradiated by a laser beams 11 that is oscillated from a laser-light source 10, focused by a lens, and introduced along the array plane from a side of the array plane. DNAs labeled by fluorescent substances of four colors are excited by the laser beam 11 and emit fluorescence, when passing through the laser-irradiation position 12. Each emitted fluorescent beam is detected by the fluorescence-detection system in a direction perpendicular to the array plane (direction perpendicular to a paper surface of FIG. 6). Inside of the capillary constitutes a channel. Accordingly, a capillary array is a type of a channel array.

Figure 7:
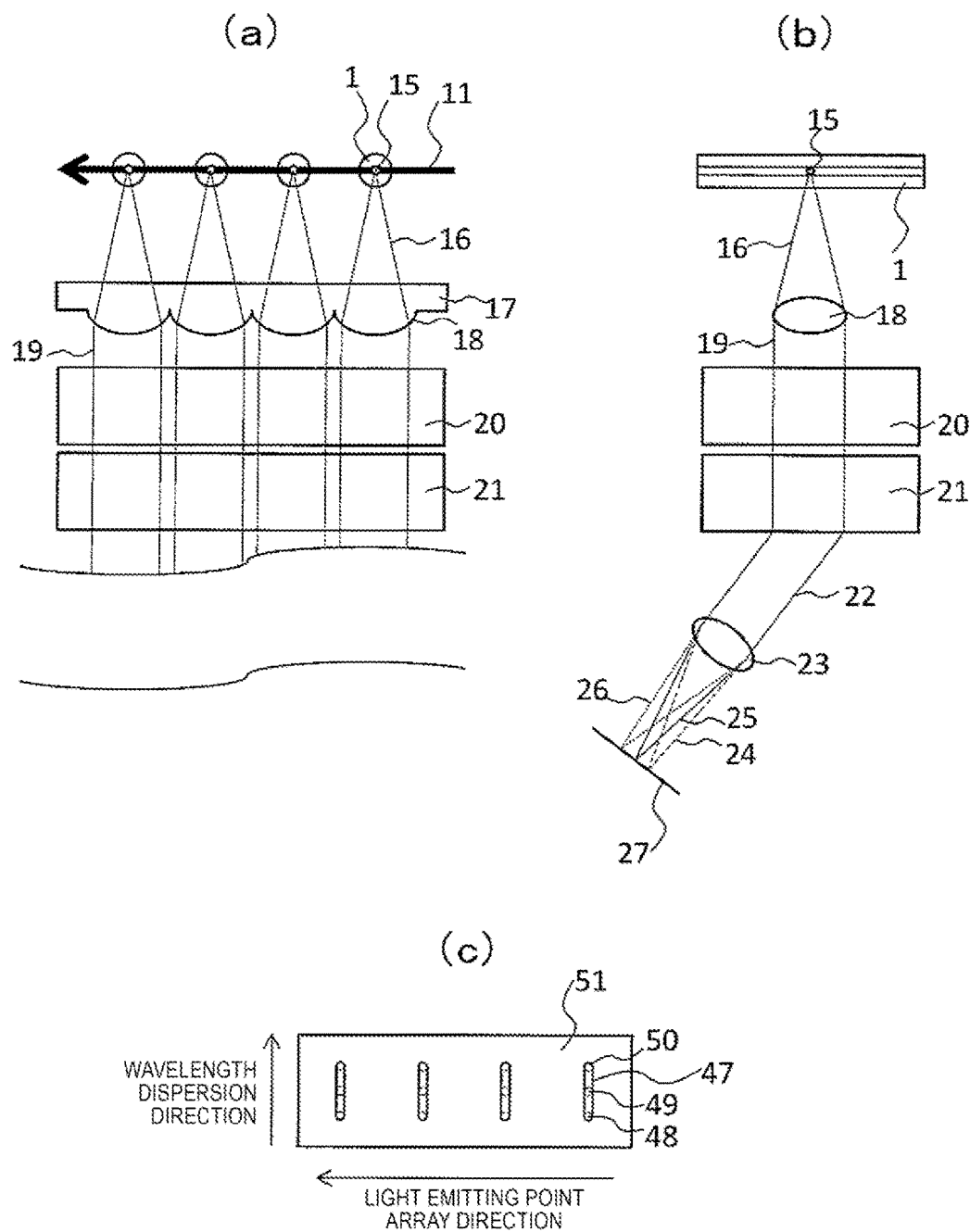
FIG. 7 is a cross-sectional schematic diagram illustrating a configuration example of a system which performs multicolor detection of light beams emitted from a light-emitting-point array by individual condensing lenses and a common wavelength-dispersion element.

FIG. 7 is a cross-sectional schematic diagram illustrating a configuration example of a system which performs multicolor detection of light beams emitted from the light-emitting-point array by individual condensing lenses and a common wavelength dispersion element. FIG. 7(a) illustrates a cross-section of the system perpendicular to the long axis of each capillary 1 at the laser-irradiation position and FIG. 7(b) illustrates a cross-section of the system parallel to the long axis of one arbitrary capillary 1. FIG. 7(c) illustrates an image 51 detected by a two-dimensional sensor 27.

As illustrated in FIG. 7, the four capillaries 1 having an outer diameter of 0.36 mm and an inner diameter of 0.05 mm are arrayed on the same plane at intervals of p=1 mm at the laser-irradiation position and the laser beam 11 with a focused diameter of 0.05 mm is incident on the side of the array plane so as to obtain a light-emitting-point array in which four (n=4) of the light-emitting points 15 with an effective diameter of d–0.05 mm are arrayed at intervals of p–1 mm. Four capillaries 1 constitute a capillary array, that is, a channel array. The entire width of the light-emitting-point array is W=p*(n–1)=3 mm. An individual-condensing-lens array 17 in which four condensing lenses 18 having the focal length of f=2 mm and the effective diameter of D=1 mm are arranged at the interval of p–1 mm is installed so that the focal-point position of each condensing lens 18 coincides with each light-emitting point 15 and the optical axis of each condensing lens 18 is perpendicular to the array plane, and light beams emitted from respective light-emitting points 15 are respectively condensed and turned into parallel-light beams 19 by the condensing lenses 18. Next, the parallel-light beams 19 are transmitted through a common long pass filter 20 disposed in parallel to the array plane in parallel so as to cut the laser light. Subsequently, the respective parallel-light beams 19 are transmitted through one common transmission-type diffraction grating 21 disposed in parallel to the array plane and having a spatial frequency of 1000 slits/mm (grating constant 1 μm) so as to be subjected to wavelength dispersion in the long axis direction of each capillary 1. An effective diameter of the transmission-type diffraction grating 21 in the direction of the light-emitting-point array and the long axis of each capillary 1 are set as DG1=5 mm and DG2=3 mm, respectively.

In this case, +1 order diffraction-light beams of 500 nm, 600 nm, and 700 nm of emitted-light beams respectively propagate in directions of 30.0°, 36.9°, and 44.4° with respect to a normal line of the array plane as illustrated in FIG. 7(b). Subsequently, an individual imaging-lens array in which four imaging lenses 23 having a focal length of f'=2 mm and an effective diameter of D'=1 mm are arrayed at intervals of p'=1 mm is installed close to the transmission-type diffraction grating 21 so that an optical axis of each imaging lens 23 is inclined at 36.9° with respect to the normal line of the array plane and coincides with the optical axis of +1 order diffraction-light beams of 600 nm to form the unmagnification images of the wavelength-dispersed parallel-light beams 22. The wavelength-dispersed parallel-light beams 22 of 500 nm, 600 nm, and 700 nm from each light-emission point 15 become condensed-light beams 24, 25, and 26 by the imaging lenses 23, respectively. Here, intervals (optical path length) between each condensing lens 18 and each corresponding imaging lens 23 is set as g=5 mm by using the wavelength-dispersed parallel-light beam 22 of 600 nm as a reference. In this case, for f=2 mm, because $-0.20*(d/D)*g+2.8*D=2.75$ mm, the equation (1) is satisfied, and the relative detected-light quantity becomes 96% (>50%). Also, because $0.95*(d/p)*g=0.24$ mm, the equation (2) is satisfied, and the crosstalk/signal intensity ratio becomes 0.4% (<25%). Furthermore, a sensor surface 27 of one common two-dimensional CCD is installed at a position 2 mm away from the imaging-lens array and in parallel to the imaging-lens array to detect wavelength-dispersed images 47 of the respective emitted-light beams 16.

FIG. 7(c) illustrates an image 51 detected by the two-dimensional CCD and respective wavelength-dispersed images 47 of the respective emitted-light beams 16 are arranged at intervals of 1 mm. The respective wavelength-dispersed images 47 include focused spots 48, 49, and 50 of the condensed light beams 24, 25, and 26 of 500 nm, 600 nm, and 700 nm, respectively. The direction of wavelength dispersion is perpendicular to the direction of the light-emitting-point array and thus, the wavelength-dispersed images 47 of respective emitted-light beams 16 do not overlap with each other and are independently detected. When a pixel size of the CCD is set as 0.05 mm×0.05 mm, wavelength resolution of an approximately 20 nm/pixel is obtained. Because unmagnification wavelength-dispersed images 47 of the respective light-emitting points 15 are formed, image sizes in a case where wavelength dispersion is not performed are 0.05 mm, that is, equals to the pixel size. That is, the image sizes do not lower wavelength resolution. In a case where four-color detection is performed, respective peak wavelengths of the four colors have intervals of 20 nm to 30 nm in a range of 500 nm to 700 nm. Because the intervals are one pixel or more on the CCD, the respective peak wavelengths are capable of being identified.

Temporal changes of the wavelength-dispersed images corresponding to respective light-emitting points, that is, temporal changes of respective wavelength-dispersion spectra are analyzed so as to obtain temporal changes in intensity of fluorescence of four colors and determine the sequences of base species, that is, the base sequences of DNAs. A length of each wavelength-dispersed image of 500 nm to 700 nm is approximately 0.5 mm and thus, it is sufficient if a size of the sensor surface of the two-dimensional CCD is 5 mm or more in the direction of the light-emitting point array and 1 mm or more in the wavelength-dispersion direction.

The entire size of the fluorescence-detection system described above is smaller than a volume (250 mm$^3$) of a rectangular parallelepiped which is specified by a width of 5 mm in a direction of the long axis of each capillary, a width of 10 mm in a direction perpendicular to the array plane, and a width of 5 mm in a direction of the light-emitting-point array. That is, compared to PTL 1, the entire size of the fluorescence-detection system is miniaturized by 1/6, 400 times. All of optical elements to be used are fine and thus, cost for manufacturing the fluorescence-detection system can be greatly reduced. Furthermore, multicolor detection sensitivity of respective emitted-light beams by the present fluorescence-detection system is high and uniform, and multicolor identification accuracy is high, and crosstalk is low. In the example described above, the number of the light-emitting point was n–4, but is not limited to the number and the same effect may be exhibited even when the number is increased. A dispersion prism may be used instead of the transmission-type diffraction grating. In the above description, although four-color fluorescence-detection and DNA sequencing by electrophoresis using a plurality of capillaries were targeted, a target of the present invention is not limited to any of the capillary, DNA sequencing, and four-color fluorescence-detection. All of cases where multicolor detection of light beams emitted from a plurality of light-emitting points is performed are included as targets.

In the matters described above, as illustrated in FIG. 7(b), an optical path of each parallel-light beam is inclined from the normal line of the array plane according to wavelength dispersion. For that reason, the two-dimensional CCD needs to be inclined with respect to the array plane and thus, according to circumstances, interference between the CCD and other elements may occur. As illustrated in FIG. 7(b), the width of the sensor surface of the CCD in the wavelength dispersion direction is desirably 1 mm or more, and although this has a lower possibility of causing the interference, interference between a circuit substrate and a casing (both are not illustrated in FIG. 7) of the CCD and other elements may be caused. For example, in the case of FIG. 7, when the entire width of the CCD in the wavelength dispersion direction exceeds 27 mm (sensor surface is assumed to be positioned at the center of the width in the wavelength dispersion direction), the CCD collides with the array plane of the capillaries. In order to avoid such a problem, it is desirable that the array plane of the capillaries and the sensor surface of the CCD are disposed in parallel.

Figure 8:
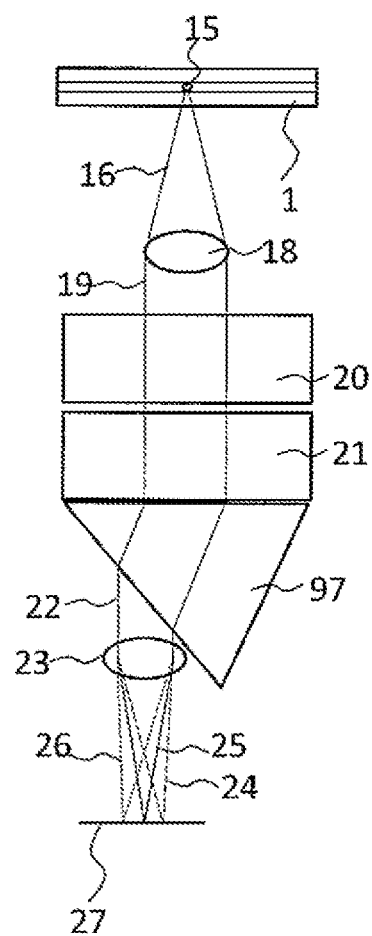
FIG. 8 is a cross-sectional schematic diagram illustrating a configuration example of a system which performs multicolor detection of light beams emitted from the light-emitting-point array by individual condensing lenses, the common wavelength-dispersion element, and a sensor disposed perpendicularly to the optical axes of the condensing lenses.

In order to achieve matters described above, a low dispersion prism 97 is disposed at the rear stage of the transmission-type diffraction grating 21 as in FIG. 8 such that each wavelength-dispersed parallel-light beam 22 transmitted through the transmission-type diffraction grating 21 and the low dispersion prism 97 propagates perpendicularly to the array plane by counterbalancing diffraction angle by the transmission-type diffraction grating 21 and refraction angle by the low dispersion prism 97. As a material of the low dispersion prism 97, glass having low dispersion is used. For example, one side of the low dispersion prism having a glass material of SK16 (nd=1.62 and vd=60.3) and an apex angle of 50° is disposed to be parallel to the array plane and close to the transmission-type diffraction grating 21. In this case, a parallel-light beam having a wavelength of 600 nm is incident on the low dispersion prism 97 at an incidence angle of 36.9° from one side thereof and is emitted at an emission angle of 50° from the other side of the low dispersion prism, that is, in a direction perpendicular to the array plane. An optical path length between each condensing lens 18 and each corresponding imaging lens 23 is set g=5 mm as it was and the relative detected-light quantity and the crosstalk/signal intensity ratio are the same as those described above. Accordingly, it is possible to allow the sensor surface 27 of the two-dimensional CCD and the array plane of the capillaries 1 to be parallel to each other while having performance equivalent to multicolor detection of FIG. 7, and it is possible to avoid interference between the two-dimensional CCD and the array plane. In such a configuration, the smaller the fluorescence-detection system, it will become more effective. Here, although the low dispersion prism 97 is disposed at the rear stage of the transmission-type diffraction grating 21, the low dispersion prism 97 may be disposed at other positions. In a case where instead of the diffraction grating, the dispersion prism is used as a wavelength dispersion element, a direct vision prism made by combining a dispersion prism and a low dispersion prism is desirable.

Figure 9:
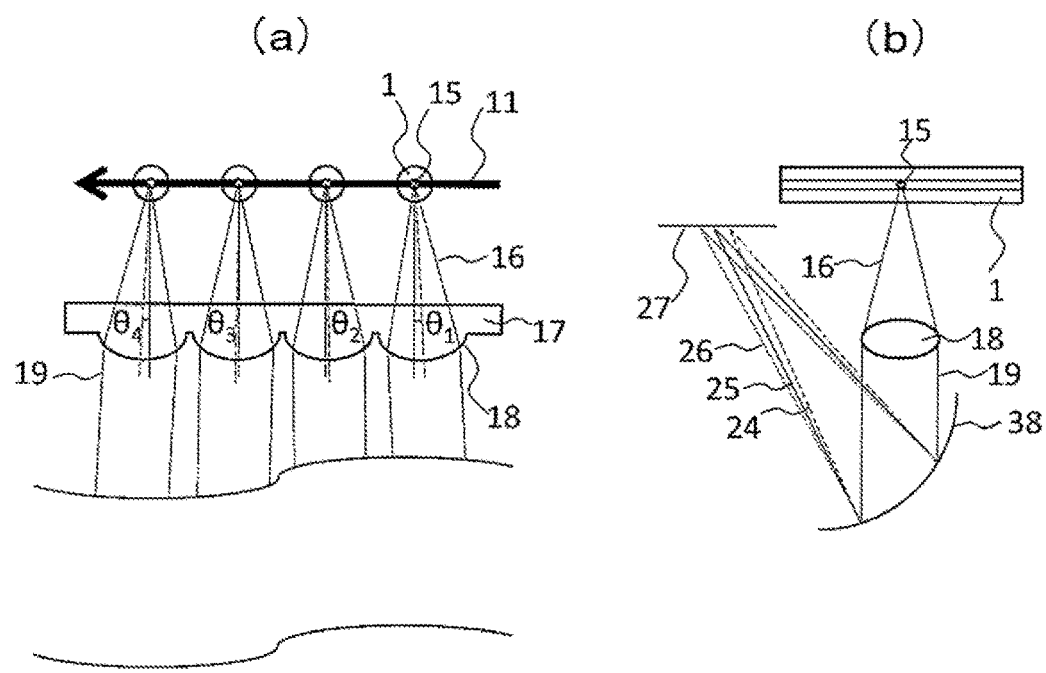
FIG. 9 is a cross-sectional schematic diagram illustrating a configuration example of a system which performs multicolor detection of light beams emitted from the light-emitting-point array by individual condensing lenses, a common concave-reflection-type diffraction grating, and a sensor disposed perpendicularly to the optical axes of the condensing lenses.

FIG. 9 is a cross-sectional schematic diagram illustrating a configuration example of a system which performs multicolor detection of light beams emitted from the light-emitting-point array by individual condensing lenses, a common concave reflection-type diffraction grating, and the sensor disposed perpendicularly to the optical axis of each condensing lens. FIG. 9(a) illustrates a cross-section perpendicular to the long axis of each capillary at the laser irradiation position and FIG. 9(b) illustrates a cross-section parallel to the long axis of one arbitrary capillary.

As illustrated in FIG. 9, when a common concave reflection-type diffraction grating 38 is used instead of the common transmission-type diffraction grating, the diffraction grating also serves as the role of the imaging lenses and thus, it is possible to omit the individual imaging-lens array and it is possible to further miniaturize the fluorescence-detection system. Also, in this configuration, the sensor surface 27 of the two-dimensional sensor and the array plane of the capillaries are disposed to be parallel to thereby make it possible to avoid interference according to miniaturization. The wavelength dispersion direction coincides with the long axis direction of each capillary, similar to the matters described above. For each condensing lens 18, although settings of the focal length f=2 mm, the effective diameter D–1 mm, and the interval p–1 mm are the same as the matters described above, the distance between each condensing lens 18 and the concave reflection-type diffraction grating 38 is set as g–2 mm and the focal length of the concave reflection-type diffraction grating 38 is set as f'=4 mm. In this case, the relative detected-light quantity is improved to 98% and the crosstalk/signal intensity ratio is reduced to 0.1%. However, in such a configuration, the imaging lens (concave reflection-type diffraction grating 38) is made common and accordingly, wavelength-dispersed images of respective emitted-light beams 16 are formed on the same position and coincide with each other on the two-dimensional sensor. Therefore, it becomes unable to independently perform multicolor detection of respective emitted-light beams 16. Here, in order to solve the problem described above, the optical axes of respective condensing lenses 18 of the individual condensing-lens array 17 are shifted between each other from a parallel to thereby shift image-forming positions of respective emitted-light beams 16.

For example, as illustrated in FIG. 9(a), angles between the optical axes of the respective condensing lenses 18 indicated by one-dot chain lines and the normal lines of the array plane indicated by solid lines are shifted from each other by 2° such that the angles are $\theta_1=3°$, $\theta_2=1°$, $\theta_3=-1°$, and $\theta_4=-3°$, and respective parallel-light beams 19 are radially spread. However, respective focal positions of respective condensing lenses 18 are disposed so as not to be shifted from respective light-emitting points 15. In this case, since the image-forming positions of respective emitted-light beams are separated from each other by a distance of 0.14 mm and the distance is larger than the imaging size of 0.1 mm (since image magnification becomes 2 times), it is possible to independently perform multicolor detection for respective emitted-light beams.

Like FIG. 7, in a case where the laser beam 11 is irradiated from the side of the array plane of the plurality of capillaries 1, laser-irradiation intensities of respective capillaries are gradually decreased toward the emission side (left side of FIG. 7(a)) of the laser beam 11 from the incidence side (right side of FIG. 7(a)) due to laser reflection at the respective capillaries. Accordingly, even when the fluorescence-detection system after the condensing lens 18 has the same efficiency for respective light-emitting points 15, fluorescence-detection intensity, or sensitivity to be obtained may become lower as the capillary 1 is positioned closer to the rear stage (left side of FIG. 7(a)). In order to eliminate non-uniformity described above, it is effective to change light-condensing efficiency of each condensing lens 18 for each light-emitting point 15. For example, it is effective to make the effective diameter of the condensing lens 18 at the incidence side of the laser beam 11 small and make the effective diameter of the condensing lens 18 at the emission side of the laser beam 11 large.

Example 2

Figure 10:
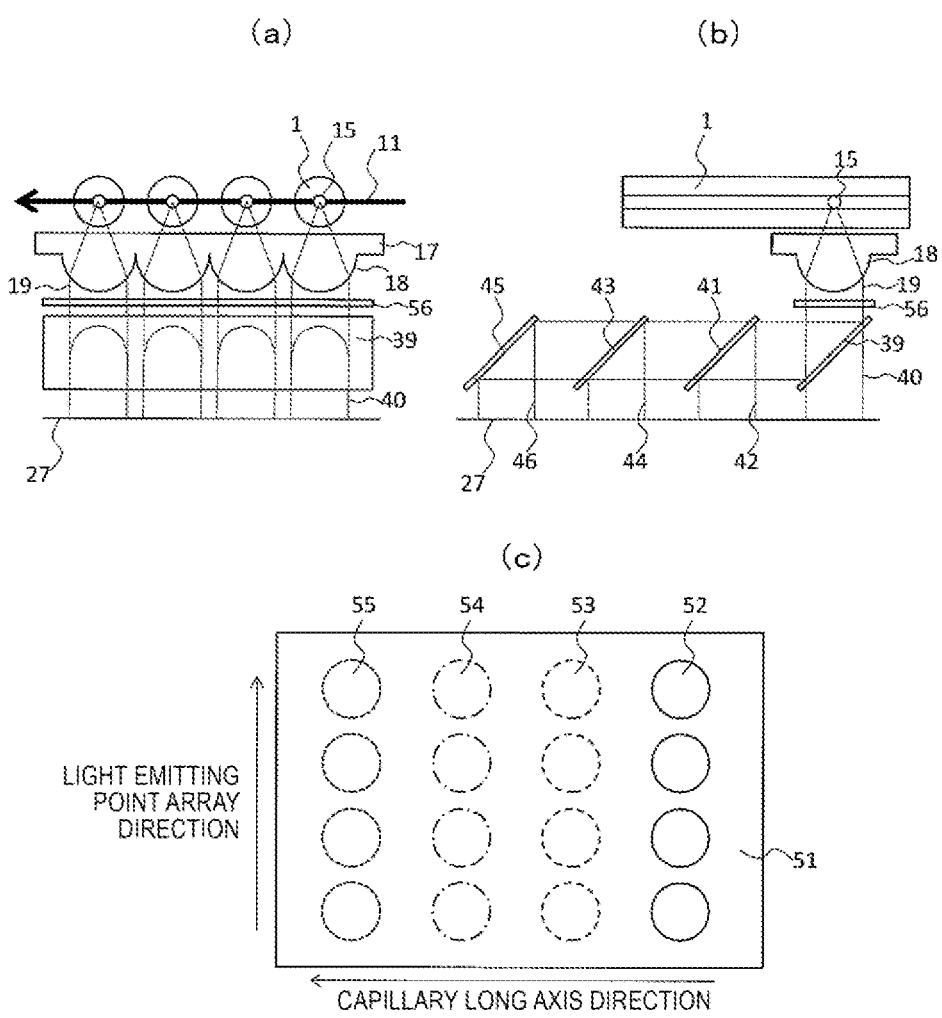
FIG. 10 is a cross-sectional schematic diagram illustrating a configuration example of a system which performs multicolor detection of light beams emitted from the light-emitting-point array by individual condensing lenses, a common dichroic-mirror set, and a sensor.

FIG. 10 is a cross-sectional schematic diagram illustrating a configuration example of a system which performs multicolor detection of light beams emitted from the light-emitting-point array by individual condensing lenses, a common series of dichroic-mirrors, and a sensor. FIG. 10(a) illustrates a cross-section perpendicular to the long axis of each capillary at the laser irradiation position and FIG. 10(b) illustrates a cross-section parallel to the long axis of one arbitrary capillary. FIG. 10(c) illustrates an image detected by the two-dimensional sensor.

As illustrated in FIG. 10, the four capillaries 1 having the outer diameter of 0.36 mm and the inner diameter of 0.05 mm are arrayed on the same plane at intervals of p=0.5 mm at the laser-irradiation positions and the focused laser beam 11 with the diameter of 0.05 mm is irradiated from the side of the array plane so as to obtain a light-emitting-point array in which the light-emitting points 15 with a number of n=4 and an effective diameter of d=0.05 mm are arrayed at the intervals of p=0.5 mm. Here, it is set that the wavelength of the laser beam 11 is 505 nm and fluorescence of four colors (light-emission maximum wavelengths) are A fluorescence (540 nm), B fluorescence (570 nm), C fluorescence (600 nm), and D fluorescence (630 nm). The entire width of the light-emitting-point array is W=p*(n−1)=1.5 mm. The individual condensing-lens array 17 in which four condensing lenses 18 having the focal length of f=1 mm and the effective diameter of D=0.4 mm are arranged at intervals of p=0.5 mm is installed so that the focal-point position of each condensing lens 18 coincides with each light-emitting point and the optical axis of each condensing lens 18 is perpendicular to the array plane, and light beams emitted from respective light-emitting points 15 are respectively condensed and turned into parallel-light beams 19.

Next, respective parallel light beams 19 are made incident in parallel on a common series of dichroic-mirrors. The series of dichroic-mirrors are composed of five elements of a long pass filter 56, an A dichroic-mirror 39, a B dichroic-mirror 41, a C dichroic-mirror 43, and a D dichroic-mirror 45 and the number of each element is one and respective elements are used being common to and in parallel for respective light-emitting points. The long pass filter 56 is parallel to the array plane and is disposed at a position 0.5 mm distance away from each condensing lens 18. Respective dichroic-mirrors 39, 41, 43, and 45 are disposed at intervals of 1 mm in parallel to the long axis of the capillaries and disposed so that the normal lines of the dichroic-mirrors are inclined at 45° with respect to the array plane. The center of the A dichroic-mirror 39 is disposed at a position 1 mm distance away from each condensing lens 18 (position 0.5 mm distance away from long pass filter 56). The size of each element is the effective diameter of DM1=3 mm in the parallel direction of the light-emitting-point array and DM2=1.4 mm (DM2=1 mm for only long pass filter) in the perpendicular direction of the light-emitting-point array.

Firstly, the respective parallel-light beams 19 are made incident vertically on the long pass filter 56 in parallel so as to cut a wavelength of 520 nm or less, especially, greatly cut 505 nm which is a wavelength of the laser beam. Next, the respective parallel-light beams transmitted through the long pass filter 56 are incident in parallel on the A dichroic-mirror 39 at 45°, and thereby light of 530 nm to 550 nm is transmitted through the A dichroic-mirror 39, and light of 560 nm or more is reflected by the A dichroic-mirror 39. The parallel-light beam of 530 nm to 550 nm is respectively called an A parallel-light beam 40 and is used mainly for detecting A fluorescence (maximum light-emission wavelength of 540 nm). The parallel-light beam of 560 nm or more is respectively incident in parallel on the B dichroic-mirror 41 at 45°, and thereby light of 560 nm to 580 nm is reflected by the B dichroic-mirror 41, and light of 590 nm or more is transmitted through the B dichroic-mirror 41. The parallel-light beam of 560 nm to 580 nm is respectively called a B parallel-light beam 42 and is used mainly for detecting B fluorescence (maximum light-emission wavelength of 570 nm).

The parallel-light beam of 590 nm or more is respectively incident in parallel on the C dichroic-mirror 43 at 45°, and thereby light of 590 nm to 610 nm is reflected by the C dichroic-mirror 43, and light of 620 nm or more is transmitted through the C dichroic-mirror 43. The parallel-light beam of 590 nm to 610 nm is called a C parallel-light beam 44 and is used mainly for detecting C fluorescence (maximum light-emission wavelength of 600 nm). Next, the parallel-light beam of 620 nm or more is respectively incident in parallel on the D dichroic-mirror 45 at 45°, and thereby light of 620 nm to 640 nm is reflected by the D dichroic-mirror 45, and light of 650 nm or more is transmitted through the D dichroic-mirror 45 (not illustrated in FIG. 10). The parallel-light beam of 620 nm to 640 nm is called a D parallel-light beam 46 and is used mainly for detecting D fluorescence (maximum light-emission wavelength of 630 nm). All of respective parallel-light beams of four sets of parallel-light beams 40, 42, 44, and 46 corresponding to each light-emitting point propagate in the direction perpendicular to the array plane. The D dichroic-mirror 45 may be replaced with a total reflection mirror.

Subsequently, the sensor surface 27 of the common two-dimensional CCD is disposed at a position 2 mm distance away from each condensing lens 18 (distance 1 mm away from the center of the respective dichroic-mirrors 39, 41, 43, and 45) in parallel to the array plane and four sets of the respective parallel-light beams 40, 42, 44, and 46 are incident on the sensor surface 27 without forming images of the four sets of the respective parallel-light beams 40, 42, 44, and 46. On an image 51 captured by the two-dimensional CCD illustrated in FIG. 10(c), four sets of respective spots 52, 53, 54, and 55 corresponding to the parallel-light beams

40, 42, 44, and 46, that is, a total of 16 spots are formed. Respective spots have a diameter of 0.4 mm, are arranged in a grating shape with 0.5 mm intervals in the direction in the light-emitting-point array and 1 mm intervals in the long axis direction of the capillary, and are independently detected. Accordingly, it is sufficient if a size of the sensor surface 27 of the two-dimensional CCD is 3 mm or more in the direction of the light-emitting-point array and 5 mm or more in the long axis direction of the capillary. In this case, when the D parallel-light beam 46 having the longest optical path length is set as a reference, the distance between each condensing lens 18 and the sensor surface 27 is g=5 mm. For f=1 mm, because $-0.20*(d/D)*g+2.8*D=1$ mm, the equation (1) is satisfied, and the relative detected-light quantity becomes 51% (>50%). Also, because $0.95*(d/p)*g=0.48$ mm, the equation (2) is satisfied, and the crosstalk/signal intensity ratio becomes 0.1% (<25%). Temporal changes in intensities of the four spots 52, 53, 54, and 55 corresponding to each light-emitting point 15 are analyzed so as to obtain temporal changes in intensities of fluorescence of four colors and determine the sequence of base species, that is, the base sequence.

The entire size of the fluorescence-detection system described above is smaller than a volume (75 mm³) of a rectangular parallelepiped which is specified by a width of 5 mm in the long axis direction of the capillary, a width of 5 mm in the direction perpendicular to the array plane, and a width of 3 mm in the direction of the light-emitting-point array. That is, compared to PTL 1, the entire size of the fluorescence-detection system is miniaturized by ½1,000 times. All of optical elements to be used are fine and thus, manufacturing cost can be greatly reduced. Furthermore, multicolor detection sensitivity of respective emitted-light beams by the present fluorescence-detection system is high and uniform, and multicolor identification accuracy is high, and crosstalk is low. In the example described above, the number of the light-emitting point was n=4, but is not limited to the number and the same effect may be exhibited even when the number is increased. Other effects caused by performing multicolor detection using the dichroic-mirrors is that compared to the diffraction grating used in PTL 1 or Example 1, effective detection-light quantity is large. In a case of using the diffraction grating, diffraction efficiency capable of being utilized in wavelength dispersion is approximately 50%, but in a case of using the dichroic-mirrors, loss almost does not occur and thus, it is possible to obtain about two times the relative detected-light quantity described above.

Figure 11:
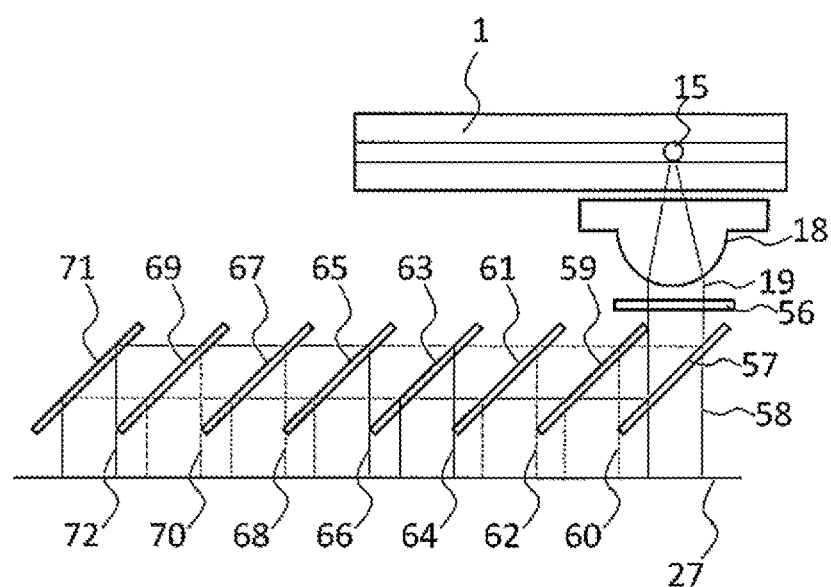
FIG. 11 is a cross-sectional schematic diagram illustrating a configuration example of a system which performs multicolor detection of light beams emitted from the light-emitting-point array, equally to a case of wavelength dispersion, by the individual condensing lenses, the common dichroic-mirror set, and the sensor.

FIG. 11 is a cross-sectional schematic diagram illustrating a configuration example of a system which performs multicolor detection of light beams emitted from the light-emitting-point array as is the case with wavelength dispersion, by individual condensing lenses, a common series of dichroic-mirrors, and the sensor.

A configuration illustrated in FIG. 11 is developed from the common series of dichroic-mirrors in FIG. 10 described above. The common series of dichroic-mirrors in FIG. 11 are composed of nine elements of the long pass filter 56 and dichroic-mirrors 57, 59, 61, 63, 65, 67, 69, and 71 arranged in order in the direction of the long axis of the capillary 1. The dichroic-mirror 57 transmits a parallel-light beam 58 of 520 nm to 540 nm and reflects light of 540 nm or more. The dichroic-mirror 59 reflects a parallel-light beam 60 of 540 nm to 560 nm and transmits light of 560 nm or more. The dichroic-mirror 61 reflects a parallel-light beam 62 of 560 nm to 580 nm and transmits light of 580 nm or more. The dichroic-mirror 63 reflects a parallel-light beam 64 of 580 nm to 600 nm and transmits light of 600 nm or more. The dichroic-mirror 65 reflects a parallel-light beam 66 of 600 nm to 620 nm and transmits light of 620 nm or more. The dichroic-mirror 67 reflects a parallel-light beam 68 of 620 nm to 640 nm and transmits light of 640 nm or more. The dichroic-mirror 69 reflects a parallel-light beam 70 of 640 nm to 660 nm and transmits light of 660 nm or more. The dichroic-mirror 71 reflects a parallel-light beam 72 of 660 nm to 680 nm and transmits light of 680 nm or more.

With matters as described above, light beam emitted from each one light-emitting point 15 forms eight spots on the sensor surface 27 and a light-emission spectrum having a resolution of 20 nm in a range spanning from 520 nm to 680 nm is produced by intensities of the eight spots for each light-emitting point 15. By adopting such a configuration, it becomes unnecessary to design and correct the dichroic-mirrors according to a kind of a fluorescent substance to be used and becomes possible to accurately detect any fluorescence in a range of 520 nm to 680 nm with high sensitivity. It is needless to say that the number of spots, which divides each emitted-light beam, and a wavelength width to be divided are not limited to the examples described above.

Example 3

Figure 12:
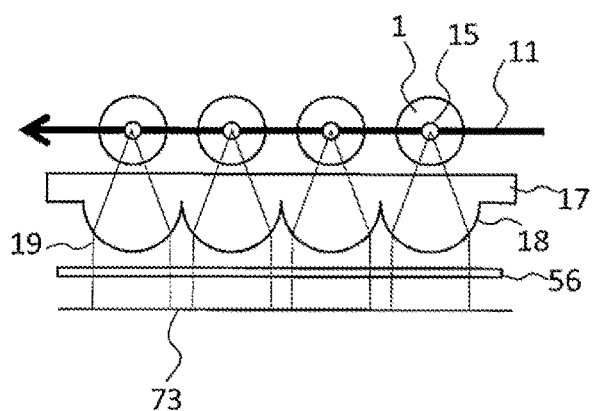
FIG. 12 is a cross-sectional schematic diagram illustrating a configuration example of a system which performs multicolor detection of light beams emitted from the light-emitting-point array by individual condensing lenses and a color sensor.
Figure 12:
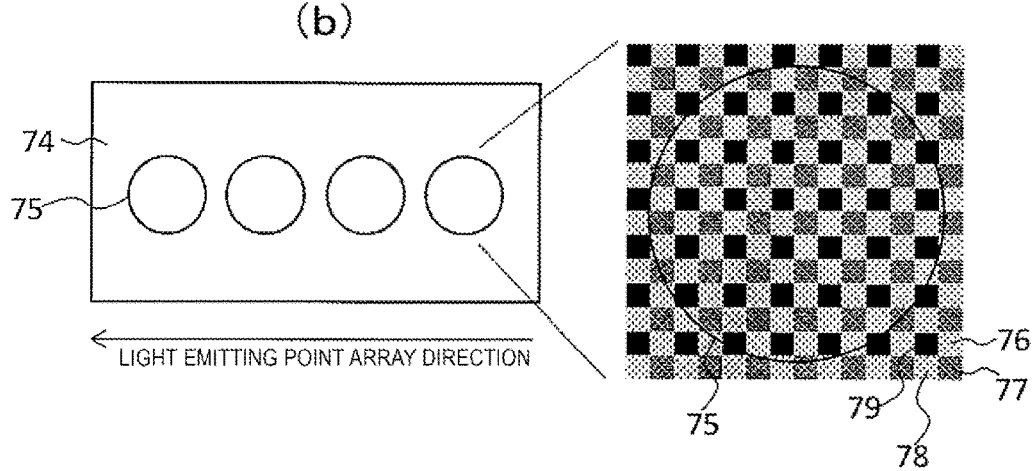

FIG. 12 is a cross-sectional schematic diagram illustrating a configuration example of a system which performs multicolor detection of light beams emitted from the light-emitting-point array by individual condensing lenses and a two-dimensional color sensor. FIG. 12(*a*) illustrates a cross-section perpendicular to the long axis of each capillary 1 at the laser-irradiation position and FIG. 12(*b*) illustrates an image detected by the two-dimensional sensor. The present example is an example in which a two-dimensional color-sensor surface 73 is used in a two-dimensional CCD.

A portion spanning from the light-emitting points 15 to the long pass filter 56 has the same configuration as that of FIG. 10 in Example 2. As illustrated in FIG. 12(*a*), respective parallel-light beams 19 transmitted through the long pass filter 56 are directly incident on the color-sensor surface 73 of the two-dimensional CCD. The distance between each condensing lens 18 and the color-sensor surface 73 is set as g=1 mm. In this case, for f=1 mm, because $-0.20*(d/D)*g+2.8*D=1.1$ mm, the equation (1) is satisfied, and the relative detected-light quantity becomes 61% (>50%). Also, because $0.95*(d/p)*g=0.10$ mm, the equation (2) is satisfied, and the crosstalk/signal intensity ratio becomes 0.0% (<25%).

As illustrated in FIG. 12(*b*), spots 75 corresponding to respective parallel-light beams 19 are formed on an image 74 of the color sensor surface 73. Respective spots 75 have a diameter of D=0.4 mm, and are arranged at intervals of 0.5 mm in the direction of the light-emitting-point array, and are therefore independently detected. As schematically illustrated in the enlarged view of FIG. 12(*b*), the color sensor surface 73 is configured in such a way that four kinds of pixels of an A pixel 76, which mainly detects A fluorescence (maximum light-emission wavelength of 540 nm), a B pixel 77, which mainly detects B fluorescence (maximum light-emission wavelength of 570 nm), a C pixel 78, which mainly detects C fluorescence (maximum light-emission wavelength of 600 nm), and a D pixel 79, which mainly detects D fluorescence (maximum light-emission wavelength of 630 nm) are respectively arranged regularly in a multitude. The size of all of the pixels 76, 77, 78, and 79 is S=0.05 mm and satisfies S<D. In this case, each spot 75 is detected with approximately 80 pixels and is detected with about 20 pixels per one kind of pixel. As such, each spot 75 is detected with a multiplicity of pixels of each kind of pixel to thereby make it possible to accurately perform multicolor detection of light beams emitted from respective light-emitting points 15. For example, it does not matter even when a relative position between each kind of pixels and the spot varies. Moreover, even when light intensity distribution within the spot is non-uniform, it is possible to uniformly detect respective colors.

The entire size of the fluorescence-detection system described above is smaller than a volume (18 mm$^3$) of a rectangular parallelepiped which is specified by a width of 3 mm in the long axis direction of the capillary, a width of 2 mm in a direction perpendicular to the array plane, and a width of 3 mm in the direction of the light-emitting-point array. That is, compared to PTL 1, the entire size of the fluorescence-detection system is miniaturized by 1/89,000 times. All of optical elements to be used are fine and thus, manufacturing cost can be greatly reduced. Furthermore, multicolor detection sensitivity of respective emitted-light beams by the present fluorescence-detection system is high and uniform, and multicolor identification accuracy is high, and crosstalk is low. In the example described above, the number of the light-emitting point was n=4, but is not limited to the number and the same effect may be exhibited even when the number is increased. However, in a case where the color sensor described above is used, use efficiency of the quantity of light incident on the sensor surface is reduced to 1/4. When it is compared to a case of approximately 50% of diffraction efficiency of Example 1 using the diffraction grating, effective efficiency becomes approximately a half. However, a configuration of the system is very simple and it is possible to further miniaturize the system.

In order to improve use efficiency of light quantity incident on the sensor surface, it is effective to use a color sensor in which elements detecting respective colors arranged perpendicular to the sensor surface, not a color sensor in which elements detecting respective colors are arranged parallel to the sensor surface as in FIG. 12. In this case, it is not necessary to satisfy S<D.

Example 4

One of the problems to be solved for mounting in the present invention is how to perform alignment of each light-emitting point and corresponding each condensing lens accurately and simply. The present example shows means for achieving the matters described above regarding a plurality of capillaries.

Figure 13:
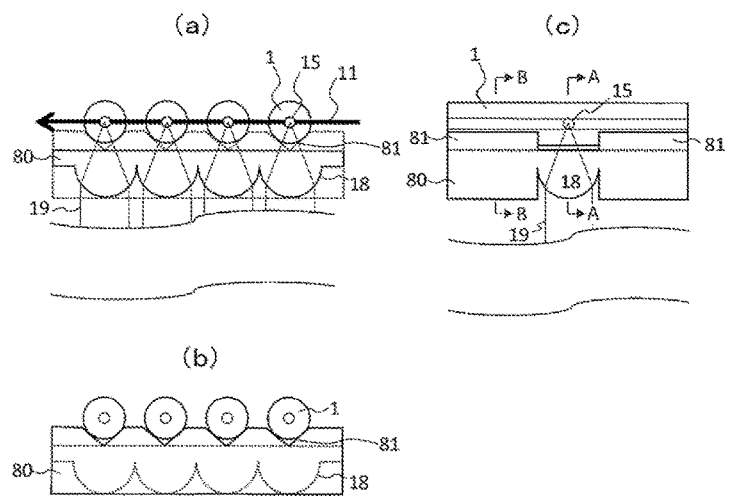
FIG. 13 is a cross-sectional schematic diagram illustrating a configuration example of a device integrated with a V-groove array, in which a plurality of capillaries are respectively arranged, and an individual-condensing-lens array.

FIG. 13 is a cross-sectional schematic diagram illustrating a configuration example of a device integrated with a plurality of capillaries, a V-groove array on which the plurality of capillaries are arranged, and an individual condensing-lens array. FIG. 13(*a*) illustrates a cross-section perpendicular to the long axis of each capillary at the laser-irradiation position, FIG. 13(*b*) illustrates a cross-section perpendicular to the long axis of each capillary at a point which is not the laser-irradiation position, and FIG. 13(*c*) illustrates a cross-section parallel to the long axis of one arbitrary capillary. FIG. 13(*a*) corresponds to a cross-section taken along the A-A line of FIG. 13(*c*) and FIG. 13(*b*) corresponds to a cross-section taken along the B-B line of FIG. 13(*c*).

The device illustrated in FIG. 13 includes a capillary array formed with a plurality of capillaries 1 and a sub-device 80. The sub-device 80 is composed of the V-groove array in which a plurality of V-grooves 81 are arranged at intervals of p and the condensing-lens array in which a plurality of condensing lenses 18 are arranged at intervals of p. The center axis of each V-groove 81 is orthogonal to the optical axis of corresponding each condensing lens 18. The plurality of capillaries 1 are respectively pushed against the V-grooves 81 to thereby make it possible to simply arrange the plurality of capillaries 1 on the same plane at the predetermined intervals of p. In the sub-device 80, the relative position between each V-groove 81 and corresponding condensing lens 18 is adjusted so that corresponding light-emitting point 15, which is an irradiation position of the laser beam 11 of corresponding capillary 1, is positioned at a focal point of the condensing lens 18. With this, light beams emitted from the light-emitting points 15 are converted into parallel-light beams 19 by the condensing lenses 18.

As illustrated in FIG. 13(*a*), in the cross-section of the capillary 1 at the light-emitting point 15, the condensing lens 18 of the sub-device 80 is present and the V-groove 81 is not present. On the other hand, as illustrated in FIG. 13(*b*), in the cross-section of the capillary 1 at both sides of the light-emitting point 15, the condensing lens 18 of the sub-device 80 is not present and the V-groove 81 is present. FIG. 13(*c*) illustrates the cross-section of the capillary 1 in the long axis direction and the condensing lens 18 is present in the center of the sub-device 80 and the V grooves 81 are present on both sides of the sub-device 80. This is devised in order not for the V-groove 81 to obstruct detection of light beams emitted from the light-emitting point 15 while achieving accurate positional alignment of the capillary 1 due to the V-groove 81. When the sub-device 80 described above is prepared in advance, it becomes possible to simply perform accurate positional alignment of each light-emitting point 15 and each condensing lens 18 by merely pushing each of the plurality of capillaries 1 against each V-groove 81. The present example can also be combined with the configuration of any of Examples 1 to 3. It is possible to integrally mold the sub-device 80, which is integrated with the V-groove array and the condensing-lens array, by processing methods such as injection molding or imprinting and manufacture the sub-device 80 at low cost and in large quantities. Also, the sub-device 80 may be completed after the V-grooves 81 and the condensing lenses 18 are separately manufactured and then combined.

The sub-device is also effective even when there is no V-groove array. For example, the surface of the capillary array side of the sub-device may be formed with a plane rather than the V-groove array. Although array intervals of the plurality of the capillaries need to be adjusted by other means, each capillary is pushed against the plane of the sub-device to thereby make it possible to control the distance between each capillary and each condensing lens, that is, the distance between each light-emitting point and each condensing lens. Alternatively, a structure for controlling the position of the capillary may be provided in the sub-device, even if it is not the V-groove.

When it is set that the focal lengths of each condensing lens 18 in the directions of the light-emitting-point array and the long axis of the capillary are f1 and f2, respectively, in the examples described above, it is set as f1=f2, but it is effective to set as f1≠f2. Each capillary 1 has a cylindrical shape and thus, has a lens function in the direction of the light-emitting-point array, but does not have a lens function in the long axis direction. Accordingly, in order to effectively condense light beams emitted from the light-emitting point 15 by the condensing lens 18, it is effective to cancel the difference of the lens functions in the two directions and to do this, it may be also effective to set as f1≠f2. This can be simply achieved by forming each condensing lens 18 with an aspherical surface. Also, each condensing lens 18 may be formed with the Fresnel lens to thereby make it possible to reduce the thickness of the lens and further miniaturize the fluorescence-detection system. Also, in the case of f1=f2, use of the Fresnel lens is effective.

Figure 14:
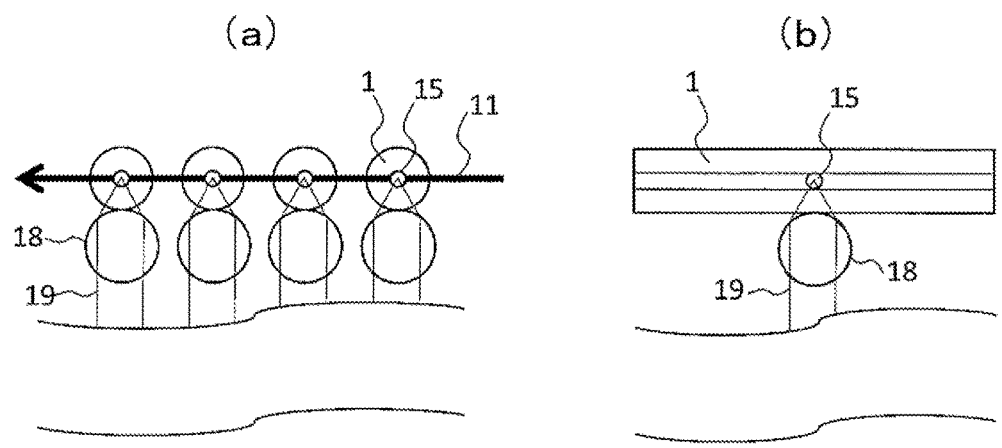
FIG. 14 is a cross-sectional schematic diagram illustrating a configuration example of a system in which individual condensing lenses are respectively adhered to the plurality of capillaries.

FIG. 14 is a cross-sectional schematic diagram illustrating a configuration example of a device in which individual condensing lenses are respectively adhered to the plurality of capillaries. FIG. 14(a) illustrates a cross-section perpendicular to the long axis of each capillary at the laser irradiation position. FIG. 14(b) illustrates a cross-section parallel to the long axis of one arbitrary capillary. Here, other methods for performing positional alignment of each light-emitting point and each condensing lens simply and accurately are shown.

Each individual condensing lens 18 is adhered to each capillary 1 so that the focal point of each condensing lens 18 coincides with each light-emitting point 15 of the capillary 1. In FIG. 14, although a spherical condensing lens 18 is used, a condensing lens having another shape may be used. Adhesion of each condensing lens 18 to each capillary 1 is preferably performed after arranging of a plurality of capillaries on the same plane is ended. This produces an effect of avoiding matters that a plurality of condensing lenses 18 are not aligned on the same plane or the optical axes of the plurality of condensing lenses 18 are not parallel to each other in an arrangement process of a plurality of capillaries 1. The capillary array which is in a state where the adhesion is ended is supplied to a user to thereby make it possible to prevent the relative position between each light-emitting point 15 and each condensing lens 18 from being shifted from a predetermined position in a transportation process of the capillary array, in a process for installing the capillary on the fluorescence-detection system, or the like.

Example 5

Figure 15:
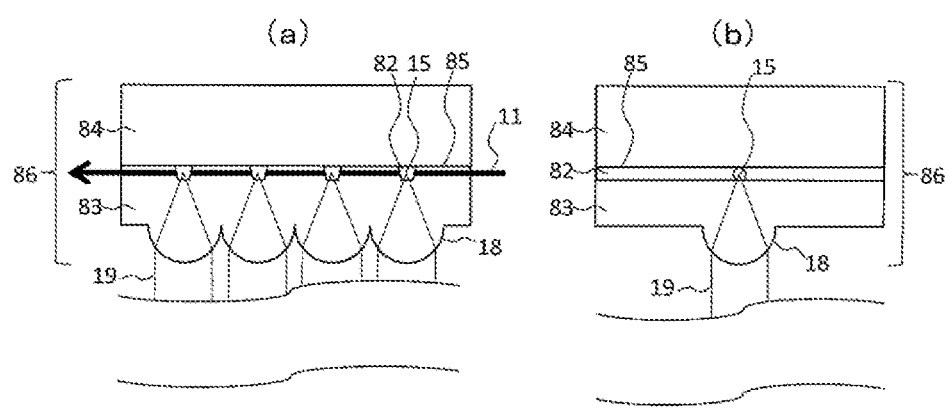
FIG. 15 is a cross-sectional schematic diagram illustrating a configuration example of a device integrated with a microchip having multichannel and the individual condensing-lens array.

FIG. 15 is a cross-sectional schematic diagram illustrating a configuration example of a device integrated with a microchip having multichannel and the individual condensing-lens array. The present example targets a plurality of channels 82, that is, a channel array provided in a microchip 86 instead of the plurality of capillaries.

The microchip 86 of the illustrated example is manufactured in such a way that a channel substrate 83 having four quadrangular grooves formed on the front surface and a flat substrate 84 of which front surface is a flat surface are laminated by allowing both front surfaces of the channel substrate 83 and the flat substrate 84 to face each other. The boundary between the channel substrate 83 and the flat substrate 84 is called a lamination surface 85. The four grooves are partitioned by the lamination surface 85 to form four channels 82. These channels 82 have a diameter of 0.05 mm and are arranged on the same plane at intervals of p=0.5 mm. In the present example, the same plane on which the plurality of channels are arrayed is simply called an array plane. The laser beam 11 of which the diameter is focused to 0.05 mm is irradiated from the side of the array plane so as to obtain a light-emitting-point array in which the light-emitting points 15 of which the number is n=4, the effective diameter is d=0.05 mm, and which are arranged at intervals of p=0.5 mm. The entire width of the light-emitting-point array is W=p*(n−1)=1.5 mm. In the present example, four individual condensing lenses 18 are formed on a rear surface located at a side opposite to the front surface on which the grooves of the channel substrate 83 are formed. The condensing lenses 18 are arranged in such a way that the condensing lenses 18 is parallel to the array plane at the interval of p=0.5 mm and each optical axis thereof is perpendicular to the array plane, and each focal point coincides with each light-emitting point.

When the channel substrate 83 is manufactured by injection molding or imprinting, it is possible to process the grooves on the front surface and the condensing lenses 18 on the rear surface at low cost while accurately aligning the relative positions as described above. Here, the focal length of the condensing lens 18 is set as f=1 mm and the effective diameter is set as D=0.4 mm. Light beams emitted from respective light-emitting points 15 are respectively condensed by the condensing lenses 18 and turned into the parallel-light beams 19. Thereafter, as described heretofore, it can also be combined with the fluorescence-detection system of any of the examples. DNA sequencing by electrophoresis may be performed using each channel 82 similar to the examples described above and it may be applied to other applications. In either case, it is possible to perform multicolor detection of light beams emitted from four light-emitting points with low crosstalk and high sensitivity by using the fluorescence-detection system which is greatly miniaturized compared to that of the related art.

Next, a more specific example using a microchip 86 will be described.

Figure 16:
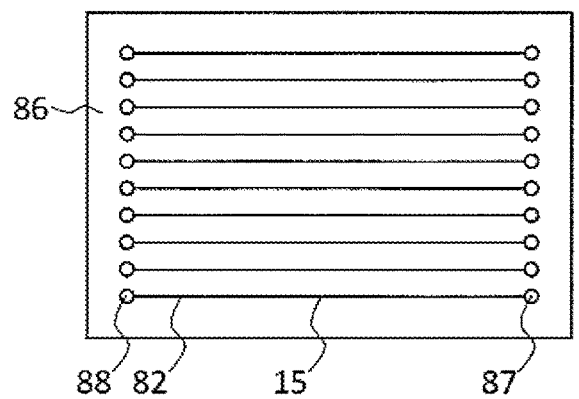
FIG. 16 is a cross-sectional schematic diagram illustrating configuration examples of a device integrated with the microchip having multichannel and the individual condensing-lens array and a system, which performs multicolor detection of light beams emitted from the light-emitting-point array by individual LED illumination, by the common dichroic-mirror set and the sensor.
Figure 16:
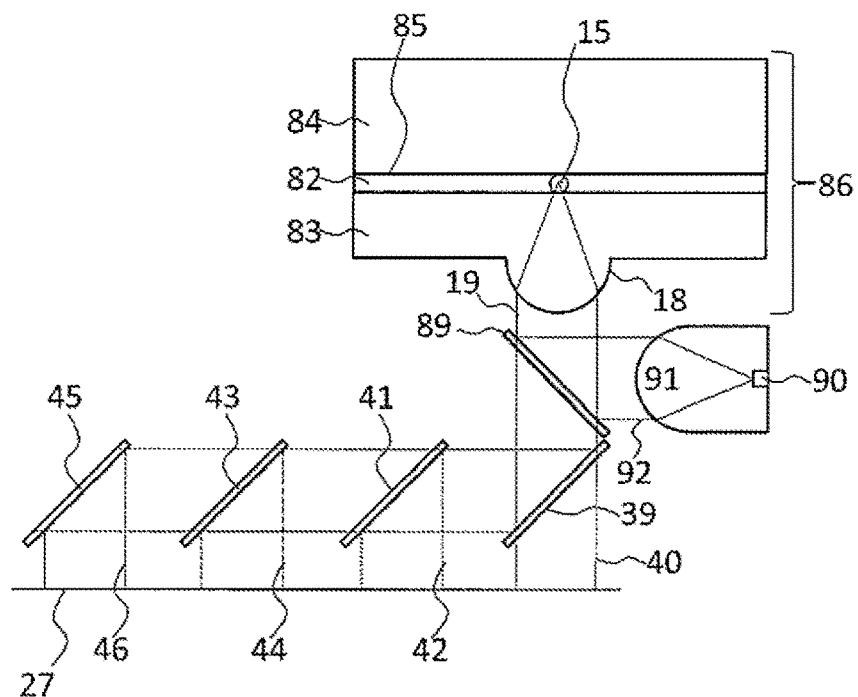
Figure 16:
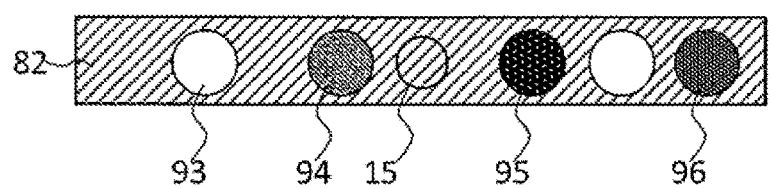

FIG. 16 is a cross-sectional schematic diagram illustrating configuration examples of a device integrated with the microchip having multi-channels and a individual-condensing-lens array and a system, which performs multicolor detection of light beams emitted from a light-emitting-point array induced by a series of individual LED illumination, by a common series of dichroic-mirrors and the sensor. FIG. 16(a) is a schematic diagram of an upper surface of the microchip, FIG. 16(b) is a schematic diagram of a cross-section of the device and the system parallel to the long axis of one arbitrary channel 82, and FIG. 16(c) is an explanatory diagram illustrating a relationship between droplets 93, 94, 95, and 96 labeled with fluorophores and flowing inside the channel 82 and the light-emitting point 15.

As illustrated in the schematic diagram of the upper surface of the microchip 86 in FIG. 16(a), ten channels 82 having the diameter of 0.1 mm and the length of 50 mm are arranged at the intervals of p=2 mm in parallel on the same plane. A flow inlet 87 and a flow outlet 88 are formed at both ends of each channel 82, respectively. The light-emitting points 15 are positioned at the center of each channel 82.

As illustrated in FIG. 16(b), in the present example, a series of LED lights are used as excitation lights instead of a laser beam and a epi-illumination fluorescence-detection optical system is adopted in the present example, unlike the examples described above. Individual LED light sources 90 correspond to respective channels 82. LED light beams having the center wavelength of 505 nm and oscillated from individual LED light sources 90 are turned into LED parallel-light beams 92 by the individual collimator lenses 91 having the focal length of 5 mm and then, are incident on a common LED dichroic-mirror 89 in parallel at an incidence angle of 45° and reflected, and propagate perpendicularly toward the array plane. The center of the LED dichroic-mirror 89 is disposed at a position 1 mm distance away from each condensing lens 18. Next, the LED parallel-light beams 92 are respectively focused on the positions of the light-emitting points 15 by the individual condensing lenses 18 having the focal length of f=1 mm and the effective diameter of D=1 mm. In this case, a size of each focused LED light is a diameter of 0.05 mm and thus, a size of each light-emitting point is also d=0.05 mm and can be made smaller than the diameter of 0.1 mm of the channel 82. This is advantageous for reducing the crosstalk.

Light beams emitted from respective light-emitting points 15 are respectively turned into the parallel-light beams 19 by the same individual condensing lenses 18 and are incident on the common LED dichroic-mirror 89 in parallel at an incidence angle of 45°, and LED light beams are respectively reflected by the LED dichroic-mirror 89, propagates in the direction toward the LED light sources 90, whereas respective fluorescent beams are transmitted through the LED dichroic-mirror 89. Thereafter, matters that respective elements of the A dichroic-mirror 39, the B dichroic-mirror 41, the C dichroic-mirror 43, and the D dichroic-mirror 45 are used in common and in parallel for each light-emitting point to detect A fluorescence, B fluorescence, C fluorescence, and D fluorescence are the same as those of Example 2. Matters different from Example 2 are that the distance between the center of the A dichroic-mirror 39 and each condensing lens 18 is 2 mm and each of the effective diameters of respective dichroic-mirrors 39, 41, 43, and 45 in the array direction of the light-emitting-point array is DM1=25 mm. In this case, the distance between each condensing lens 18 and the sensor surface 27 is g=6 mm. For f=1 mm, because $-0.20*(d/D)*g+2.8*D=2.74$ mm, the equation (1) is satisfied, and the relative detected-light quantity becomes 362% (>50%). Also, because $0.95*(d/p)*g=0.14$ mm, the equation (2) is satisfied, and the crosstalk/signal intensity ratio becomes 0.0% (<25%).

In the present example, the microchip 86 and the fluorescence-detection system are used for digital PCR measurement. In the digital PCR, a large number of droplets (emulsion) are formed in oil and a target DNA molecule is not included in or only one target DNA molecule is included in each droplet. In this state, the PCR is performed and in a case where the target is present and is subjected to amplification, fluorescence is emitted. The number of molecules present in the original sample is accurately quantified by examining whether each droplet emits fluorescence or not. Furthermore, fluorescence-detection of four colors is performed to thereby make it possible to independently perform the digital PCR regarding four kinds of targets. One of the problems to be solved by the digital PCR is to improve throughput, and high throughput multicolor detection of a large number of droplets is important. FIG. 16(c) illustrates a configuration in which four kinds of droplets 93, 94, 95, and 96 respectively labelled by A fluorophore, B fluorophore, C fluorophore, and D fluorophore together with oil flow inside the channel 82 and fluorescence is emitted in response to excitation received when crossing the light-emitting point 15. Although in the related art, the digital PCR measurement is performed by one-color detection using one channel, in the present example, the digital PCR measurement is performed by four-color detection using ten channels and thus, throughput becomes 40 times. Furthermore, the microchip 86 and the fluorescence-detection system are extremely small in size and can be manufactured at low costs.

The present invention is not limited to the embodiments described above and includes various modifications. For example, the examples described above are described in detail in order to make the present invention easier to understand and is not necessarily limited to an embodiment in which all configuration described are included. Also, it is possible to replace a portion of a configuration of an example with a configuration of another example and it is possible to add a configuration of another example to a configuration of a certain example. Also, it is possible to add, delete, and replace of a configuration of another configuration, with respect to a portion of a configuration of a certain example.

REFERENCE SIGNS LIST

1: capillary
10: laser light source
11: laser beam
12: laser irradiation position
15: light-emitting point
17: condensing lens array
18: condensing lens
20: long pass filter
21: transmission-type diffraction grating
23: imaging lens
27: sensor surface
28: sensor area
38: concave reflection-type diffraction grating
39: A dichroic-mirror
41: B dichroic-mirror
43: C dichroic-mirror
45: D dichroic-mirror
47: wavelength-dispersed image
56: long pass filter
73: color sensor surface
80: sub-system
81: V-groove
82: channel
83: channel substrate
84: flat substrate
86: microchip
90: LED light source
91: collimator lens
97: low dispersion prism

The invention claimed is:

1. A multicolor detection system comprising:
   a condensing-lens array having a plurality of condensing lenses that individually condense light beams respectively emitted from a light-emitting-point array having a plurality of light-emitting points;
   a common dichroic mirror set on which the condensed light beams are respectively incident in parallel, the dichroic mirror set including at least two different dichroic-mirrors that divide the condensed light beams; and
   a common sensor on which the divided light beams from the common dichroic mirror set are respectively incident in parallel without being condensed.

2. The multicolor detection system according to claim 1, wherein the sensor is one two-dimensional sensor and a sensor surface of the two-dimensional sensor is substantially perpendicular to each optical axis of the condensing lenses.

3. The multicolor detection system according to claim 1, wherein an array direction of the dichroic-mirrors is perpendicular to each of an array direction of the light-emitting points and an optical axis direction of the condensing lenses.

4. The multicolor detection system according to claim 1, further comprising:
   a channel array in which at least part of a plurality of channels are arrayed on a same plane; and
   a light source configured to irradiate the channels with light, wherein the light-emitting points are located inside the respective channels by irradiating each of the channels with light from the light source.

5. The multicolor detection system according to claim 4, wherein the plurality of channels are inside a plurality of capillaries, respectively, and
a focal length of the condensing lenses in a direction of the light-emitting-point array is different from a focal length in a direction perpendicular to the direction of the light-emitting-point array and the optical axes direction of the condensing lenses.

6. The multicolor detection system according to claim 1, further comprising:
a channel array in which at least part of a plurality of channels are arrayed on a same plane; and
a laser light source configured to irradiate the channels with a laser beam,
wherein the light-emitting points are located inside the respective channels by irradiating each of the channels with the laser beam incident from a side of the channel array and parallel to the same plane, and
a light-condensing efficiency of the condensing lenses corresponding to the channels increases as the channels are separated away from a laser-beam-incident side of the channel array.

7. The multicolor detection system according to claim 1, further comprising:
a channel array in which at least part of a plurality of channels are arrayed on a same plane;
a light source configured to irradiate the channels with light,
wherein the light-emitting points are located inside the respective channels by irradiating each of the channel with light from the light source; and
a device integrated with the channel array in which at least part of the plurality of channels are arranged on the same plane and the condensing-lens array.

8. The multicolor detection system according to claim 7, wherein the plurality of channels are inside a plurality of capillaries, respectively, and
the multicolor detection system further comprises:
a substrate having formed on a front surface thereof a groove array in which a plurality of grooves for holding the plurality of capillaries are arrayed and having on a rear surface thereof the condensing lens array.

9. The device according to claim 7, wherein the plurality of channels are inside one microchip and the condensing-lens array is integrated with the microchip.

10. A multicolor detection system comprising:
a condensing-lens array having a plurality of condensing lenses that individually condense light beams respectively emitted from a light-emitting-point array having a plurality of light-emitting points; and
at least one common sensor on which the condensed light beams are respectively incident in parallel,
wherein each light-emitting point has a finite size, and
when it is set that an average effective diameter of the light-emitting points is d, an average focal length of the condensing lenses is f, an average effective diameter of the condensing lenses is D, and an average optical distance between each condensing lens and the sensor is g, $$f \leq -0.20*(d/D)*g+2.8*D$$

is satisfied.

11. The multicolor detection system according to claim 10, further comprising:
a channel array in which at least part of a plurality of channels are arrayed on a same plane; and
a light source configured to irradiate the channels with light,
wherein the light-emitting points are located inside the respective channels by irradiating each of the channels with light from the light source.

12. The multicolor detection system according to claim 10,
wherein when an average array interval of the light-emitting points is set as p, $$f \geq 0.95*(d/p)*g$$

is satisfied.

13. The multicolor detection system according to claim 10, further comprising:
a channel array in which at least part of a plurality of channels are arrayed on a same plane;
a light source configured to irradiate the channels with light,
wherein the light-emitting points located inside the respective channels by irradiating each of the channels with light from the light source; and
a device integrated with the channel array in which at least part of the plurality of channels are arranged on the same plane and the condensing-lens array.

14. A multicolor detection system comprising:
a condensing-lens array having a plurality of condensing lenses that individually condense light beams respectively emitted from a light-emitting-point array having a plurality of light-emitting points; and
at least one common sensor on which the condensed light beams are respectively incident in parallel,
wherein each light-emitting point has a finite size, and
when it is set that an average effective diameter of the light-emitting points is d, an average focal length of the condensing lenses is f, an average array interval of the light-emitting points is p, and an average optical distance between each condensing lens and the sensor is g, $$f \geq 0.95*(d/p)*g$$

is satisfied.

15. The multicolor detection system according to claim 14, further comprising:
a channel array in which at least part of a plurality of channels are arrayed on a same plane; and
a light source configured to irradiate the channels with light,
wherein the light-emitting points are located inside the respective channels by irradiating each of the channels with light from the light source.

16. A multicolor detection system comprising:
a condensing lens array having a plurality of condensing lenses that individually condense light beams respectively emitted from a light-emitting-point array having a plurality of light-emitting points;
an imaging lens array in which a plurality of imaging lenses, that turn the light beams individually into focused light beams, respectively; and
at least one common sensor on which the focused light beams are respectively incident in parallel,
wherein each light-emitting point has a finite size, and
when it is set that an average effective diameter of the light-emitting points is d, an average focal length of the condensing lenses is f, an average effective diameter of the condensing lenses is D, and an average optical distance between each condensing lens and the imaging lens corresponding to the condensing lens is g, $$f \leq -0.20*(d/D)*g+2.8*D$$

is satisfied.

17. The multicolor detection system according to claim 16, further comprising:
   a channel array in which at least part of a plurality of channels are arrayed on a same plane; and
   a light source configured to irradiate the channels with light,
   wherein the light-emitting points are located inside the respective channels by irradiating each of the channels with light from the light source.

18. The multicolor detection system according to claim 16,
   wherein when an average array interval of the light-emitting points is set as p, $$f \geq 0.95*(d/p)*g$$

is satisfied.

19. A multicolor detection system comprising:
   a condensing-lens array having a plurality of condensing lenses that individually condense light beams respectively emitted from a light-emitting-point array having a plurality of light-emitting points;
   an imaging-lens array in which a plurality of imaging lenses, that turn the light beams individually into focused light beams, respectively; and
   at least one common sensor on which the focused light beams are respectively incident in parallel,
   wherein each light-emitting point has a finite size, and
   when it is set that an average effective diameter of the light-emitting points is d, an average array interval of the light-emitting points is p, an average focal length of the condensing lenses is f, and an average optical distance between each condensing lens and the imaging lens corresponding to the condensing lens is g, $$f \geq 0.95*(d/p)*g$$

is satisfied.

20. The multicolor detection system according to claim 19, further comprising:
   a channel array in which at least part of a plurality of channels are arrayed on a same plane; and
   a light source configured to irradiate the channels with light,
   wherein the light-emitting points are located inside the respective channels by irradiating each of the channels with light from the light source.

* * * * *